United States Patent
Zougman

(10) Patent No.: US 11,009,510 B2
(45) Date of Patent: May 18, 2021

(54) METHOD AND DEVICE FOR PROTEIN PREPARATION

(71) Applicant: University of Leeds, Leeds (GB)

(72) Inventor: Alexandre Zougman, Leeds (GB)

(73) Assignee: THE UNIVERSITY OF LEEDS, Leeds (GB)

(*) Notice: Subject to any disclaimer, the term of this patent is extended or adjusted under 35 U.S.C. 154(b) by 0 days.

(21) Appl. No.: 15/031,544

(22) PCT Filed: Oct. 23, 2014

(86) PCT No.: PCT/GB2014/053162
§ 371 (c)(1),
(2) Date: Apr. 22, 2016

(87) PCT Pub. No.: WO2015/059478
PCT Pub. Date: Apr. 30, 2015

(65) Prior Publication Data
US 2016/0266137 A1 Sep. 15, 2016

(30) Foreign Application Priority Data

Oct. 24, 2013 (GB) ..................................... 1318840

(51) Int. Cl.
*G01N 33/68* (2006.01)
*C07K 1/36* (2006.01)

(52) U.S. Cl.
CPC ........... *G01N 33/6842* (2013.01); *C07K 1/36* (2013.01)

(58) Field of Classification Search
None
See application file for complete search history.

(56) References Cited

U.S. PATENT DOCUMENTS

| | | | |
|---|---|---|---|
| 5,702,699 A * | 12/1997 | Hanisch | C07K 14/565 424/85.6 |
| 2001/0034066 A1 | 10/2001 | Alam | |
| 2004/0033224 A1* | 2/2004 | Van Holten | A23J 3/12 424/140.1 |
| 2007/0082004 A1* | 4/2007 | Morton | C07K 1/30 424/178.1 |
| 2008/0193981 A1* | 8/2008 | Fahrner | C07K 1/32 435/70.21 |
| 2008/0287661 A1 | 11/2008 | Jones | |
| 2013/0172539 A1* | 7/2013 | Miyagi | C07K 1/145 530/412 |

FOREIGN PATENT DOCUMENTS

| | | |
|---|---|---|
| DE | 102005001362 | 7/2006 |
| WO | 2004041848 | 5/2004 |
| WO | 2008005455 | 1/2008 |
| WO | 2011149942 | 12/2011 |
| WO | 2013166605 | 11/2013 |

OTHER PUBLICATIONS

Zhang, Q. et al. 2009. Sensitive determination of kaempferol in rat plasma by high-performance liquid chromatography with chemiluminescence detection and application to a pharmacokinetic study. Journal of Chromatography B 877: 3595-3600. specif. p. 3595.*
Wisniewski, J.R. et al. 2009. Universal sample preparation method for proteome analysis. Nature Methods 6(5): 359-363 and Supplementary Data, specif, pp. 359, 361 and Supplementary Protocols in Supplementary Data.*
Yeung, Y.-G. et al. 2008. Removal of detergents from protein digests for mass spectrometry analysis. Analytical Biochemistry 382: 135-137. specif, pp. 135; 136, 137.*
Putnam, F.W. et al. 1944. The precipitation of proteins by synthetic detergents. Journal of the American Chemical Society 66(5): 692-697. specif, pp. 692, 693, 696.*
Manza, L.L. et al. 2005. Sample preparation and digestion for proteomic analyses using spin filters. Proteomics 5: 1742-1745. specif, pp. 1742, 1743, 1745.*
GE Healthcare. 2010. Strategies for Protein Purification Handbook, [retrieved on Jan. 4, 2019], Retrieved from the internet: https://cdn.gelifesciences.com/dmm3bwsv3/AssetStream.aspx?mediaformatid=10061&destinationid=10016&assetid=15680. pp. 1-167.*
Wisniewski, J.R. et al. 2009. Universal sample preparation method for proteome analysis. Nature Methods 6(5): 359-362. specif. p. 360.*
Wisniewski, J.R. et al. 2009. Universal sample preparation method for proteome analysis. Nature Methods 6(5): 359-363.w Supplementary Data (SD) pp. 1-24. specif, pp. 359, 360, 363; SD, pp. 20-22.*
Sigma-Aldrich. Microcon centrifugal filter unit. YM-10 & YM-3 membranes, NMWCO 10kDa & MWCO 3kDa. Retrieved on Jul. 24, 2020. Retrieved from the internet: <https://www.sigmaaldrich.com/catalog/product/sigma/[z648078? or z648051?]lang=en&region=US> pp. 1-4. specif, pp. 1 and 3.*
Puchades, M. et al. 1999. Removal of sodium dodecyl sulfate from protein samples prior to matrix-assisted laser desorption/ionization mass spectrometry. Rapid Communications in Mass Spectrometry 33: 344-349. specif, p. 344.*

(Continued)

*Primary Examiner* — Renee Claytor
*Assistant Examiner* — Sharon M. Papciak
(74) *Attorney, Agent, or Firm* — Ping Wang; Morris, Manning & Martin LLP

(57) ABSTRACT

The present invention provides a method of preparing a sample comprising one or more proteins of interest, the method comprising: providing a sample comprising a population of proteins of interest solubilised with a surfactant in a medium; exposing said sample to a mild precipitant to cause precipitation of said proteins; during or after the precipitation step, bringing said sample into contact with a matrix adapted to capture said precipitated proteins and prevent excessive aggregation of precipitated protein particles; and washing the matrix with captured precipitated proteins to remove the surfactant. A sample preparation device to carry out the same is also provided.

1 Claim, 11 Drawing Sheets

(56) References Cited

OTHER PUBLICATIONS

Yigzaw, Y. et al. 2006. Exploitation of adsorptive properties of depth filters for host cell protein removal during monoclonal antibody purification. Biotechnology Progress 22: 228-296. specif, pp. 288, 289.*
Anonymous: "Micro-Adsorptive Sample Preparation for Mass Spectrometry" Jan. 2003 (Jan. 1, 2003), Retrieved from the Internet: URL:157.93.252.5/publications.nsf/a73664f9f981af8c852569b9005b4eee/e47abe34d9aa4dab85256cd100561e33/$FILE/PS5175EN00.pdf [retrieved on Jan. 16, 2015].
Usd et al: "P-series Depth Filter Sheets Optimized for Low Extractables, Endotoxins and Beta Glucans", Jan. 11, 2010 (Jan. 11, 2010), pp. 1-4, Retrieved from the Internet:URL: www.pall.com/pdfs/Biopharmaceuticals/09-3915_USD2205d_P-Series.pdf [retrieved on Jan. 16, 2015].
Anonymous et al: "FTechnical Note TN228 : Enrichment of Phosphopeptides Before MALD1-T0F and Nanoelectrospray MS Using ZipTipMC Pipette Tips",Feb. 27, 2001, Retrieved from the Internet: URL: www.emdmillipore.com/NL/en/prod uct/,MM_NF-05737#documentation [retrieved on Jan. 16, 2015].
Gertrude E. Perlmann: "Combination of Proteins and Metaphosphoric Acid", J. Biol. Chem., Oct. 16, 1940, pp. 707-711, vol. 1941, Issue 137, Retrieved from the Internet: URL: www.jbc.org/content/137/2/707.full.pdf [retrieved on Jan. 15, 2015].
Farid E. Ahmed: "Sample preparation and fractionation for proteome analysis and cancer biomarker discovery by mass spectrometry",Journal of Separation Science,Feb. 12, 2009.
Alexandre Zougman et al: "Suspension trapping (STrap) sample preparation method tor bottom-up proteomics analysis", PROTEOMICS, Mar. 26, 2014, pp. 1000-1006, vol. 14, No. 9 & Alexandre Zougman et al: "Supplementary Experimental Methods to "Suspension trapping (STrap) sample preparation method for bottom-up proteomics analysis"", Proteomics 2014, Nr. 14, May 1, 2014 (May 1, 2014), pp. 1006-1010, XP055162706, Retrieved tom the Internet: URL:onlinelibrary.wiley.com/store/10.1002/pmi c.201300553/asset/supinfo/pmic7693-sup-0001-SuppMat.pdf.
Clement Bordier: "Phase Separation of Integral Membrane Proteins in Trition X-114 Solution" , The Journal of Biological Chemistry, Feb. 25, 1981, pp. 1604-1607, vol. 256, Issue 4.
Jurgen Cox & Matthias Mann: "MaxQuant enables high peptide identification rates, individualized p.p.b.-range mass accuracies and proteome-wide protein quantification" J; Nature Biotechnology, Dec. 2008, pp. 1367-1372, vol. 26, No. 12.
Jurgen Cox, Nadin Neuhauser, Annette Michalski, Richard A. Scheltema, Jesper V. Olsen, and Matthias Mann: "Andromeda: A Peptide Search Engine Integrated into the MaxQuant Environment," Proteome Res., Jan. 21, 2011, pp. 1794-1805, vol. 10.
Serena Di Palma, Shabaz Mohammed & Albert J R Heck: "ZIC-cHILIC as a fractionation method for sensitive and powerful shotgun proteomics" Nature Protocols, Oct. 25, 2012, pp. 2041-2055, vol. 7 No. 11.
Gilar, M., Olivova, P., Daly, A. E., Gebler, J.: "Two-dimensional separation of peptides using RP-RP-HPLC system with different pH in first and second separation dimensions," Journal of Separation Science, 2005, pp. 1694-1703, vol. 28, Issue 4.
Jan Havlis, Henrik Thomas, Marek Sebela, and Andrej Schevchenko: "Fast-Response Proteomics Accelerated In-Gel Digestion of Proteins," Analytical Chemistry, Mar. 15, 2003, pp. 1300-1306, vol. 75, No. 6.
Chandra Sekhar Rao Kadiyala, Sara E. Tomechko, Masaru Miyagi: "Perfluorooctanoic Acid for Shotgun Proteomics" PLoS ONE, Dec. 2010, pp. 1-7, vol. 5, Issue 12.
U.K. Laemmli: "Cleavage of Structual Proteins during the Assembly of the Head of Bacteriophage T4," Nature Aug. 15, 1970, pp. 680-685, vol. 227.
Pascal Loyer, et al.: "Characterization of Cyclin L1 and L2 Interactions with CDK11 and Splicing Factors" The Journal of Biological Chemistry, Mar. 21, 2008, pp. 7721-7732, vol. 283, No. 12.
Intellectual Property Office search report, Priority App. No. GB1318840.4, dated Apr. 24, 2014.
Andrej Schevchenko et al.: "Mass Spectrometric Sequencing of Proteins from Silver-Stained Polyacrylamide Gels," et al., Analytical Chemistry, Mar. 1, 1996, pp. 850-858, vol. 68, No. 5.
Donald F. Summers, et al.: "Evidence for Virus-Specific Noncapsid Proteins in Poliovirus-Infected hela Cells" Biochemistry, Jun. 21, 1965, pp. 505-513, vol. 54.
Jacek R. Wisniewski, et al.: "Universal sample preparation method for proteome analysis" Nature Methods, May 2009, pp. 359-363, vol. 6, No. 5.
Wisniewski et al.: "Spin filter-based sample preparation for shotgun proteomics" Nature Methods, Nov. 2009 pp. 785, vol. 6, No. 11.
Jacek R. Wisniewksi et al.: "Proteomic workflow for analysis for archival formalin-fixed and paraffin-embedded clinical samples to a depth of 10,000 proteins," Proteomics Clin. Appl., 2013. pp. 225-233, vol. 7.
Ying-Qing Yu, et al.: Enzyme-Friendly, Mass Spectormetry-Compatible Surfactant for In-Solution Enzymatic Digestion of Proteins, Analytical Chemistry, Nov. 1, 2003, pp. 6023-6028, vol. 75, No. 21.
Yaoyang Zhang, et al.: "Protein Analysis by Shotgun/Bottom-up Proteomics" NIH Public Access Author Manuscript, Chem Rev., Apr. 10, 2013, pp. 2343-2394.
Hu Zhou, et al.: "Proteomic reactors and their applications in biology," FEBS Journal, 2011, pp. 3796-3806, vol. 278.
Jana Svačinová, A new approach for cytokinin isolation from *Arabidopsis* tissues using miniaturized purification: pipette tip solid-phase extraction; Plant Methods, 2012, 8:17.
Alexandre Zougman, Blog from forum share proteomics, Mar. 10, 2014, pp. 1-1, XP055456956.
European Patent Office; Office Action Communication pursuant to Article 94(3) EPC; dated Jan. 22, 2019, Application No. 14790275.3-1111, Ref. DD/P210742EP.
European Patent Office; Office Action Communication pursuant to Article 94(3) EPC; dated Mar. 15, 2018, Application No. 14790275.3-1111, Ref. DD/P210742EP.

* cited by examiner

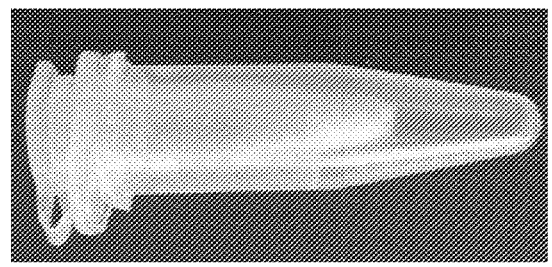
b Assembled Spin-unit
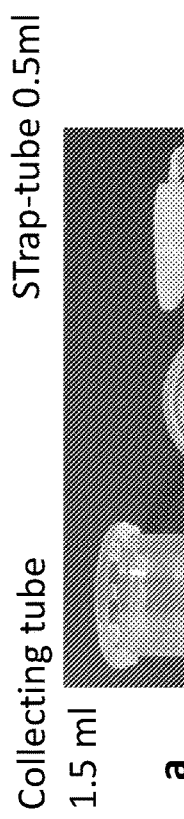
a  Collecting tube 1.5 ml / STrap-tube 0.5ml / Adapter lid
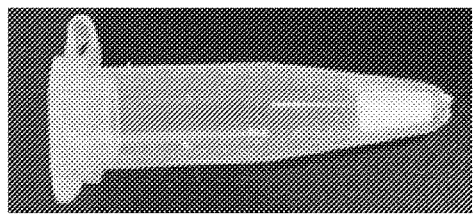
STrap-tube  c
Four holes are punctured in the lid's middle part with a 25G needle
— Quartz
═ $C_{18}$
Two holes are punctured in the tube's bottom with a 25G needle
Fig 8

METHOD AND DEVICE FOR PROTEIN PREPARATION

CROSS-REFERENCE TO RELATED APPLICATIONS

The present application is a 35 U.S.C. Section 371 national stage filing of International Patent Application No. PCT/GB2014/053162, filed 23 Oct. 2014, and through which priority is claimed to UK application GB 1318840.4, filed 24 Oct. 2013, the disclosures of which are incorporated herein by reference in their entireties.

The present invention relates to methods and devices for the preparation of samples containing proteins. Particularly, but not exclusively, it relates to the preparation of samples of proteins which contain a surfactant for subsequent analysis by mass spectrometry.

BACKGROUND OF THE INVENTION

A typical bottom-up proteomic experiment is based on tryptic proteolysis with subsequent characterization of the generated peptide products by mass spectrometry (MS)[1]. In order to obtain a thorough map of proteins, detergents (surfactants), amphipathic by nature, which facilitate solubilisation of hydrophobic proteins, are deployed.

Most charged or ionisable molecules interfere with the ionisation of the analyte (i.e. compete for charges) and cause signal suppression and/or elevation of the background noise, and thus the following should be avoided:
Salts: Na+, Cl−, Tris, etc.
Chaotropes: Urea, Thiourea, Gu-HCl, etc.
Detergents/surfactants: SDS, NP-40, Triton X, octyl glucoside, TWEEN, etc.
Polymers: PEG, Ampholytes, etc.
Non-volatile, ionic compounds: glycerol, DMSO, etc.

It can be seen that conventional detergents, which are required to extract hydrophobic proteins (e.g. membrane bound proteins) are not compatible with mass spectrometry and must be eliminated from the samples prior to MS analysis. Sodium dodecyl sulfate (SDS), an anionic surfactant, is the most widely used detergent for protein separation and solubilisation. The most common analytical utility of SDS is in separation of proteins by means of polyacrylamide gel electrophoresis (SDS-PAGE)[5]. The protein-containing gel bands may be cut out and in-gel digestion performed[6]. However, the overall value of this procedure for proteome profiling and quantitation is limited due to such adverse effects as partial protein digestion, artifactual modifications, poor peptide recovery and the difficulties in processing of large numbers of gel bands if large-scale comparative profiling across multiple samples is needed.

During recent years, the Filter Aided Sample Preparation Method (FASP) has gained popularity as one of the key tools for gel-free proteomic processing of the cellular and tissue SDS-extracted material[7]. The FASP method, however, is very time-consuming, dependent on batch-to-batch reliable performance of the commercial spin-filter units, requires careful implementation and control to prevent drying-out or damage of the spin-filter membrane, and is disconnected from the clean-up step.

There remains a need for a simple, efficient and reproducible sample preparation tool, compatible with small sample amounts, which would combine the proven power of the SDS-based protein extraction with rapid detergent removal, protein digestion and in-situ clean-up of the peptides.

STATEMENTS OF THE INVENTION

According to a first aspect, the present invention provides a method of preparing a sample comprising one or more proteins of interest, the method comprising:
providing a sample comprising a population of proteins of interest solubilised with a surfactant in a medium;
exposing said sample to a mild precipitant to cause precipitation of said proteins;
during or after the precipitation step, bringing said sample into contact with a matrix adapted to capture said precipitated proteins and prevent excessive aggregation of precipitated protein particles; and
washing the matrix with captured precipitated proteins to remove the surfactant.

It is preferred that the matrix is a porous or fibrous material which is able to be penetrated by the medium comprising the proteins. Furthermore, the matrix should be a suitable material to permit the precipitated proteins to be reversibly captured by the matrix.

The presence of such a matrix is very important as it allows for aggregation of the protein to be moderated. If there was no such matrix present, the precipitated proteins would tend to aggregate together in an uncontrolled manner. This is undesirable as it makes further processing of the proteins more difficult or impossible. For example, digestion of the proteins with a protease is impeded without aggregates first being disrupted by a chaotropic agent such as concentrated urea.

Furthermore, having the protein precipitate captured in the matrix allows for washing (rinsing) of the matrix and proteins to be performed to remove the surfactant, and potentially other contaminants, whilst ensuring the protein is not lost or diluted excessively, which would make further processing problematic.

There are many materials which are potentially suitable for use as a matrix in the present invention, and therefore it is not possible to define a specific set of materials. Various exemplary suitable materials, and general properties of such materials, will be described below, but it will be apparent to the skilled person that other materials can be used.

Particularly preferred matrixes comprise depth filter materials.

Depth filters are a type of filters that use a porous filtration medium to retain particles throughout the medium, rather than just on the surface of the medium (as is the case with membrane/surface filters). Depth filters are commonly used when the fluid to be filtered contains a high load of particles because, relative to other types of filters, they can retain a large mass of particles before becoming clogged (for more information on depth filters, and other filters, see Derek B Purchas and Ken Sutherland, Handbook of Filter Media (2nd Edition), Elsevier Advanced Technology (2002)).

Depth filters typically have a random network of pore channels that vary in size and geometry. They are manufactured from a variety of solid materials. Materials of construction include various forms of quartz, polymers, cellulose, and glass, either singly or in combination. The processes used to manufacture depth filters do not result in a regular arrangement of the solid matrix. Instead, there is a range of pore sizes within a given structure that includes pores significantly larger and significantly smaller than the nominal pore rating.

Depth filters are typically made out of one or more of the following materials:
Quartz;
Glass fibre;
Polymers; and
Cellulose.

Preferred depth filters for use in the present invention are formed from quartz, glass fibre or polymers. The filter material should typically be inert with respect to the proteins and reagents used in the method, so that undesirable reactions are avoided.

As touched on above, depth filters are not characterised by a defined pore size in the same way as membrane filters (surface filters), and the pore size is typically highly variable. Thus it is imprecise to define a specific pore size for a depth filter-based matrix. Depth filters are often referred to in terms of target particle size retention, e.g. 5 µm, 1 µm or the like.

The key consideration in the context of the present invention is that the matrix (typically a depth filter) is able to bind and retain the proteins during subsequent washing steps and maintain them in a form such that a protease can be used to digest them into fragments without requiring treatment with a chaotropic agent such as urea, typically required in the art where precipitated protein particles have excessively aggregated. This can be assessed for any putative matrix by testing it in a protocol as described in the examples below. This is a straightforward and routine process for the skilled person, and allows the skilled person to identify alternative suitable matrix materials.

Typically, the matrix is un-modified. However, in certain embodiments, the matrix may be modified. For example, the matrix may be chemically modified.

By way of general guidance, the un-modified matrix typically:
- is adapted to capture and retain fine and very fine particles, e.g. from several micrometers (e.g. 10 µm or less, 5 µm or less, or 2 µm or less) to sub-micrometer size range (e.g. down to 0.2 µm or even 0.1 µm in size);
- is substantially inert with respect to the proteins in the sample;
- is able to reversibly capture (i.e. retain) proteins from the sample;
- allows a protease to digest the proteins in situ; and
- does not bind to, and therefore retain, the surfactant to any significant extent.

Particularly preferred depth filters for the present invention include quartz depth filters, e.g. those available under the brand names MK360 (Munktell), AQFA (Millipore), QM-A (Whatman), and borosilicate glass filters, e.g. those available under the name GF/D (Whatman).

By 'capture', 'retain' and related terms in the context of the matrix and protein/protein fragments it is meant that the matrix and protein interact such that the protein is retained in the matrix during or shortly after the precipitation step and subsequent washing steps. The interaction is typically non-covalent, and may be an intermolecular interaction or simple retention on the basis of size. However, in some embodiments, the interaction may be covalent. The specific nature of the interaction is not critical. What is important is that the matrix can retain the protein following precipitation, allows the surfactant to be washed away, prevents excessive aggregation and allows the protein material to be eluted afterwards. In the case of a size-based retention, i.e. where protein particles are trapped in pores because of their size, elution may be achieved by digesting the protein so that it is broken into protein fragments of smaller size (peptides). An alternative or additional approach may involve denaturing the proteins/peptides to remove secondary and/or tertiary structures and thus allow the matter to change shape and thus pass through pores which were too small prior to digestion/denaturation.

The capacity (and hence volume) of the matrix should generally be sufficient to trap substantially all of the proteins in the sample without becoming clogged. However, it will be apparent that the required capacity depends, inter alia, on the concentration of the proteins in the sample. Suitable matrix volumes can be determined by trial and error, and typically there will be no problem encountered if a higher volume of matrix is provided than is strictly required, other than it may require more reagents to wet, wash, and digest proteins, and to elute the resultant peptides.

As set out above, the precipitant is preferably a 'mild' precipitant. A mild precipitant causes the protein solubilised with surfactant to precipitate to form a suspension of fine particles of protein. It does not, however, cause severe precipitation which renders the precipitated protein insensitive to protease digestion (e.g. with trypsin or LysC), especially under aqueous conditions.

Conventional methods for precipitating proteins in preparation for mass spectrometry are harsh and cause dramatic precipitation and aggregation of the proteins which render them rather insensitive to protease activity. Exemplary precipitants in prior art methods include trichloroacetic acid (TCA), typically a 100% w/v solution (500 g TCA into 350 ml $dH_2O$). See, for example Curr Protoc Protein Sci. 2010 February; CHAPTER: Unit-16.12. Typically, such precipitated proteins are treated with strong chaotropic agents to render them susceptible to protease action. Exemplary chaotropic agents for such purposes include urea (e.g. at 8M concentration) and the like.

The present invention can involve the use of buffers and the like which could be considered to be mildly chaotropic. For example, a preferred buffer for the present invention is based upon methanol and Tris. However, such agents have only negligible chaotropic effect on precipitated and aggregated proteins, quite unlike urea.

Suitably the mild precipitant comprises an acid. Phosphoric acid has been determined experimentally to be a highly suitable precipitant. For example, exposing the SDS-solubilised protein to phosphoric acid at a concentration of from 0.9 to 1.5% w/v is typically effective. Preferably the concentration of phosphoric acid is from 1.0 to 1.4% w/v, more preferably from 1.1 to 1.3% w/v, yet more preferably from 1.15 to 1.25% w/v.

For the avoidance of doubt, in the present case, as is typically the case in the art, 'phosphoric acid' refers to trihydroxidooxidophosphorus phosphoric acid (IUPAC nomenclature), more commonly shortened to orthophosphoric acid. However, other 'phosphoric acids', called polyphosphoric acids can also be suitable for use in the present invention at suitable concentrations.

To obtain the appropriate concentration of precipitant, typically a comparatively concentrated solution of the precipitant is added to the sample and thereby diluted. For example, to an 18 µL sample, 2 µL of 12.15% phosphoric acid can be added to obtain a final concentration of 1.22% w/v.

Other acidic precipitants can be used, provided they are compatible with the methods of the present invention, which can readily be assessed by the skilled person. For example, other relatively weak inorganic acids can be used.

Other methods of precipitating proteins may also be suitable for the present invention. For example, salts can be used to drive 'salting out' precipitation.

The suitability of any precipitant for use in the present invention can be tested using the methodology described below. In particular, any precipitant should be able to precipitate proteins which have been solubilised with a surfactant (typically SDS), but the precipitate so formed should be capable of being digested with a protease (typically trypsin) without treatment with a strong chaotropic agent (e.g. urea). As mentioned above, the precipitate will typically aggregate over time and this will lead to protease no longer being effective. Accordingly, protease sensitivity should be assessed immediately after precipitation, or, ideally, following capture of the precipitate in a depth filter immediately after precipitation. Furthermore, the precipitant should not prevent downstream analysis of the proteins/ protein fragments (peptides) using mass spectrometry.

The precipitated sample is then typically brought into contact with the matrix, although precipitation could potentially be conducted in the presence of the matrix.

Where the precipitated sample is added to the matrix after precipitation has been commenced, typically the matrix is already permeated with a fluid medium (phase), e.g. a buffer solution. Preferably the fluid medium which permeates the matrix is mildly chaotropic. For example it can comprise an aqueous solution of a short chain alcohol, e.g., methanol, ethanol or propanol. Most preferred is an aqueous methanolic solution, e.g. comprising 60% or higher methanol, typically around 90% methanol.

An exemplary, and generally preferred, buffer solution is the 'STrapping buffer' described below.

It is believed that the combination of a mild acidic precipitation step (e.g. using phosphoric acid, as described above) followed by addition to a mildly chaotropic buffer (e.g. an aqueous methanolic buffer such as the 'STrapping buffer') provides extremely favourable conditions for the method of the present invention. It allows highly protease-sensitive protein particles to be efficiently captured for subsequent washing and digestion.

The step of washing the matrix with captured precipitated proteins to remove the surfactant uses a suitable washing liquid in which the SDS is soluble. A suitable liquid is an aqueous methanolic solution, e.g. the 'STrapping buffer'. However, other liquids would be suitable, and the suitability of any putative washing liquid could be readily tested. Typically mild chaotropes are useful for this purpose.

In some situations it may be desirable to remove the washing liquid, e.g. where presence of that liquid might have an adverse effect on the activity of a subsequently administered protease. Water or an ammonium bicarbonate solution can be used for this purpose.

One exemplary method comprises a washing step using an aqueous methanolic solution to remove SDS, and the second rinse to remove residual methanolic solution, e.g. using water or an aqueous ammonium bicarbonate solution.

Preferably the method comprises:
exposing the matrix with protein particles captured thereon to a protease to generate fragments of the proteins.

Typically the protease is administered after the SDS, or other surfactant, has been washed away.

The protease is typically trypsin or LysC, but it can be any other suitable protease, e.g. chymotrypsin, AspN, GluC, or ArgC. For example, 0.03-0.10 µg/µl of trypsin (03708985001, Roche or V5111, Promega) in 40-50 mM ammonium bicarbonate can be used in embodiments of the invention.

Typically, suitable proteases are an endopeptidase (i.e. the protease cuts within the protein chain, rather than just at the terminal residues), and have a short recognition sequence. For example, the short recognition sequence may be one or two amino acids in length. Examples of suitable proteases and their respective recognition sequences are shown in Table 1.

TABLE 1

| Protease | Specificity |
| --- | --- |
| Trypsin | Carboxyl side of Arg and Lys |
| Lys-C | Carboxyl side of Lys |
| Asp-N | Amine side of Asp |
| Glu-C | Carboxyl side of Glu and Asp |
| Arg-C | Carboxyl side of Arg |
| Chymotrypsin | Carboxyl side of Tyr, Phe, Trp and Leu |

Suitable proteases typically are active in moderate conditions, such as at room temperature or at elevated temperatures, such as 35-47° C., and at pH 6.5-9.0, for example.

The protease is typically added to the medium permeating the matrix.

It is a significant advantage of the present invention that proteins can be digested with proteases in situ in the matrix, and without the need for the use of strong chaotropic agents, such as urea.

Digestion of the proteins with a protease is a conventional step in the preparation of proteins for analysis by mass spectrometry.

When proteins are brought into contact with the matrix, the proteins are typically either retained within the matrix at a pore that is smaller than the protein, or due to non-specific interactions between the proteins and the matrix. Once the protein is digested within the matrix by a protease, the resulting protein fragments are typically sufficiently small to pass readily through the pores of the matrix, and/or the non-specific interactions between the protein fragments and the matrix are reduced sufficiently to allow the protein fragments to be eluted from the matrix for analysis.

However, in some embodiments the surface of the matrix may be modified to change the affinity of the surface of the matrix for one or more amino acids of the protein/protein fragments. The surface of the matrix may be modified to increase the affinity of the surface for one or more amino acids of the proteins/protein fragments. The surface of the matrix may be modified to decrease the affinity of the surface for one or more amino acids of the proteins/protein fragments.

Accordingly, in embodiments where the affinity of the surface of the matrix is modified to increase the affinity of the surface for one or more amino acids of the proteins/ protein fragments, the proteins/protein fragments may bind to the matrix specifically. For example, a covalent bond may be formed between one or more amino acids of the proteins/ protein fragments and the modified matrix. Advantageously, the specific binding of proteins/protein fragments to the matrix may allow certain proteins/protein fragments that can specifically bind to the matrix to be separated from other proteins/protein fragments that cannot bind to the matrix.

The surface of the matrix may be modified by treating the surface with an agent that reacts with the surface to change at least some of the chemical groups at the surface of the matrix. The surface may be modified by treating the surface with an agent that adsorbs to the surface of the matrix and thereby changes at least some of the chemical groups at the surface of the matrix with the chemical groups of the adsorbed agent.

In some embodiments, the surface of the matrix may be modified to increase the affinity of the surface of the matrix for hydrophilic residues of proteins/protein fragments. In other embodiments, the surface of the matrix may be modified to increase the affinity of the surface of the matrix for hydrophobic residues of proteins/protein fragments.

For example, in embodiments where the matrix comprises a silica based material such as quartz or glass, the surface of the matrix may be treated with a functionalised silane. The functionalised silane may be an amino silane, or an amine terminal silane, such that the surface of the matrix when treated with the functionalised silane comprises at least some amine groups. The functionalised silane may be a thio silane, or a thiol terminal silane, such that the surface of the matrix when treated with the functionalised silane comprises at least some thiol groups. The functionalised silane may be an epoxy silane or an epoxy terminal silane, such as (3-Glycidyloxypropyl)trimethoxysilane, for example, such that the surface of the matrix when treated with the functionalised silane comprises at least some epoxy groups.

It will be readily appreciated by those skilled in the art that a practical method of modifying the surface of the matrix may be achieved via an intermediate modification of the surface of the matrix. For example, in embodiments where the matrix is silica based, the surface of the matrix may be initially modified to comprise amine groups, and then those amine groups may then be further modified to comprise alternative groups, such as dithiols, or epoxy groups, for example. Alternatively, in embodiments where the surface of the matrix has been initially modified to comprise epoxy groups, those epoxy groups could be further modified to comprise amine modified aptamers against a specific amino acid residue, such as L-arginine. In further embodiments where the surface of a matrix has been modified to comprise epoxy groups, those epoxy groups could be further modified with an amino boronic acid to increase the affinity of the surface of the matrix for glycopeptides. Accordingly, the required functionality of the surface of the matrix may be more practically achieved in a multi-step process.

In embodiments where the surface of the matrix has been modified to comprise sulphur containing groups, the sulphur containing groups typically specifically bind to available cysteine residues within the proteins/protein fragments as they pass through the matrix. Therefore, the surface of the matrix may be modified to increase the affinity of the surface of the matrix for cysteine residues of the proteins/protein fragments, such that the cysteine residue-containing proteins/protein fragments may be separated selectively from the proteins/protein fragments that do not contain cysteine residues. For example, the surface of the matrix may be modified to comprise pyridyldithiol groups. Accordingly, available cysteine residues of the proteins/protein fragments will covalently bind to the surface as the proteins/protein fragments pass through the matrix, and may subsequently be removed from the matrix by treatment with a reducing agent such as dithiothreitol (DTT). In this way, the method of the present aspect may allow fractionation of the proteins/protein fragments within a sample by selectively binding to those proteins/protein fragments comprising at least one cysteine residue at the surface of the proteins/protein fragments.

Suitably the method comprises the step of desalting the proteins or peptide fragments. Desalting can be achieved by rinsing the proteins or peptide fragments with salt free buffer and/or water.

Preferably the method comprises:
eluting the proteins or fragments thereof from the matrix.
The proteins or protein fragments can be eluted using any suitable agent. Basic solutions (e.g. ammonium bicarbonate), or acidic solutions (e.g. trifluoroaceric acid) or salt solutions (e.g. sodium chloride) and, as such, are suitable for eluting the proteins/fragments from the matrix.

The eluted proteins or protein fragments suitably pass to a secondary matrix.

Suitably the secondary matrix is a hydrophobic matrix, e.g. a stationary hydrophobic phase suitable for reverse phase chromatography (RPC). The most common RPC matrices are based upon silica substrates, for example, silica with alkyl chains bonded thereto, but any inert hydrophobic solid phase could, in theory, be used. A particularly preferred hydrophobic matrix comprises octadecyl carbon chain ($C_{18}$)-bonded silica, $C_8$-bonded silica, or a combination of the two, but other suitable matrices include cyano-bonded silica and phenyl-bonded silica.

The secondary matrix can have several roles, e.g.:
it functions as a mechanical support for the primary matrix,
it acts as a guard filter to capturing stray particles and shed fibre material from the primary matrix, and
it assists in the final clean-up of the peptides; and
it can allow for chromatographic resolution of the protein fragments.

The method may further comprise eluting the protein fragments from the secondary matrix using a suitable elution solution, e.g. 70% acetonitrile, 0.5% formic acid in $H_2O$.

In some preferred embodiments the method comprises the step of eluting the protein fragments from a hydrophobic, secondary matrix using a series of eluents or gradient of eluent of increasing hydrophobicity. Thus the method can provide a degree of chromatographic separation of the protein fragments based on their hydrophobicity. This allows the population of protein fragments to be resolved on the basis of hydrophobicity which can aid in later analysis. For this purpose a secondary matrix comprising $C_8$-bonded silica is very useful. A suitable series of eluents comprises, consecutively, 5% ACN in water, 10% ACN in water, 15% ACN in water and then 60% acetonitrile in 0.5% formic acid (FA); such a series allows for four peptide fractions to be obtained.

Preferably the method is performed, at least in part, in a medium comprising methanol. A particularly preferred medium is a buffer comprising methanol (typically 60% or higher v/v methanol) and Tris-HCl at an approximately neutral pH (e.g. from 6.5 to 7.5), e.g. 90% methanol in 100 mM Tris-HCl, pH 7.1. Such a medium is referred to in the examples below as the 'STrapping buffer'. Other suitable media will be suitable for the present invention will be apparent to the skilled person.

During the initial loading of the matrix with precipitated protein, the typical working ratio between the STrapping buffer and the acidified sample is approximately 6:1, with the typical range being 4.5:1 to 7:1.

The present method is suitable for processing samples which comprise many conventional surfactants. SDS is commonly used as a surfactant for solubilizing and extracting membrane bound proteins from cells, but other surfactants are also used, including sodium cholate, sodium deoxycholate, n-dodecyl-beta-D-maltoside, Triton X-114, NP-40 (Thermo Scientific), and Brij 35 (Thermo Scientific).

Suitably the method is a method of preparing a sample containing proteins solubilised with a surfactant for analysis by mass spectrometry, e.g. LC-MS/MS.

Suitably the method is a method of preparing a sample containing proteins for proteomic analysis. Such method typically involves lysis of cells and extraction of proteins. A suitable lysis medium comprises 5% (w/v) sodium dodecyl sulphate (SDS), 50 mM Tris-HCl, pH 7.6.

The sample may be serum or plasma, and therefore, the method may not require the step of lysis of cells to extract proteins. According to the invention, the serum or plasma sample may be exposed to a mild precipitant and the resulting precipitate removed before the supernatant is prepared using the method of the present invention.

The step of exposing the sample to a mild precipitant may precipitate out of solution some of the more abundant serum or plasma proteins, such as albumin, for example, and allow the less abundant serum proteins to be subject to proteomic analysis by subsequently processing them using the method of the present aspect. Accordingly, in embodiments where the sample is serum or plasma, the method of the invention may include the step of removing some or the majority of the precipitated, more abundant proteins from the sample before bringing the sample into contact with the matrix. Therefore, the method may allow proteomic analysis of the proteins found in serum or plasma without requiring the preliminary serum or plasma depletion procedures typically required to remove the most abundant proteins that may interfere with the process of identifying proteins that are of low abundance in serum or plasma.

The sample may comprise a reducing agent prior to the step of introducing the mild precipitant. Accordingly, precipitation of some of the more abundant proteins may be induced in the presence of the mild precipitant and a reducing agent.

Accordingly, the method may be a method of preparing a serum or plasma sample comprising one or more proteins of interest, the method comprising providing a serum or plasma sample comprising a population of proteins of interest solubilised with a surfactant medium; exposing said sample to a mild precipitant to cause precipitation of said proteins; during or after the precipitation step, bringing said sample into contact with a matrix adapted to capture said precipitated proteins and prevent excessive aggregation of precipitated protein particles; and washing the matrix with captured precipitated proteins to remove the surfactant.

Serum or plasma samples, for example, typically comprise a large amount of proteins, and the abundance of each of these proteins greatly varies. This disparity in abundance of these proteins has previously required the concentration of the highly abundant proteins, such as serum albumin, to be greatly reduced by harsh or time consuming preliminary depletion methods.

Surprisingly, the inventors have found that by carrying out a mild precipitation step prior to using the method of the present aspect on the supernatant, a larger number of proteins can be identified in the resulting serum when compared to undepleted serum (i.e. serum that has not been processed in a prior mild precipitation step), without requiring the harsh preliminary depletion procedures known in the art.

Suitably the method comprises the step of reducing the disulphide bonds of proteins. This can be achieved by known techniques, including the use of dithiothreitol (DTT), preferably under denaturing conditions. Suitably, DTT is provided at a concentration of 20 mM and the mixture is heated up at 95° C. for 5 min to denature the proteins and allow DTT to react with cysteine residues. DTT can also be used to prevent intramolecular and intermolecular disulphide bonds from forming between cysteine residues of proteins.

Suitably the method comprises the step of alkylation of cysteine residues in the proteins/protein fragments, e.g. using 0.9 M iodoacetamide in $H_2O$ to a final concentration of 150 mM, or any other suitable reagent. This prevents formation of disulphide bonds between cysteine residues.

Suitably centrifugation is performed to drive the various media, reagents, buffers and the like through the matrix (matrices) as required.

Alternatively, pumps or the like can be used to move the various media, reagents, buffers and the like through the matrix (matrices) of the present invention.

According to a second aspect, the present invention provides a sample preparation device for proteins in a liquid medium, the device comprising a vessel having an inlet and an outlet, a matrix disposed between the inlet and the outlet, the matrix being adapted to capture and retain particles of precipitated protein from a medium as is flows from the inlet to the outlet.

Suitably the matrix is formed from a depth filter material, as discussed above.

Suitably the matrix extends across the entire lumen of the vessel such that anything flowing from the inlet to the outlet must pass through at least a portion of the matrix.

Preferably the device comprises a secondary matrix, preferably a hydrophobic matrix disposed between the primary matrix and the outlet, i.e. downstream of the primary matrix.

Various secondary matrices are discussed above.

Suitably the secondary matrix extends across the entire lumen of the vessel such that anything flowing from the inlet to the outlet must pass through at least a portion of the secondary matrix.

The outlet may lead to a sump or reservoir adapted to collect various media, reagents, buffers and the like which pass through the matrix.

Preferably the device is a modified pipette tip. However, other types of vessels are contemplated, e.g. vessels adapted for automated and/or high throughput sample preparation.

Where the device is a pipette tip it preferably comprises a layer of primary matrix and a layer of secondary matrix, the layers being arranged such that the primary matrix is upstream of the secondary matrix relative to the net direction of flow through the tip. Typically the primary and secondary matrices are provided in the tapered portion of the tip, with the secondary matrix being located nearer to the narrow tip end (nozzle), and the primary matrix being located nearer to the wide end.

Typically the primary and/or secondary matrix each comprises one or more flat layers (e.g. disks for a vessel which is circular in cross section) of the relevant material (e.g. depth filter or hydrophobic silica). Two or more layer of the relevant material can be stacked to provide the desired total depth, and hence volume and capacity, of matrix.

The matrices can be retained in the device in any suitable manner, e.g. mechanically (e.g. by friction with the wall of the device, or using a clip, frame or other support means) or by an adhesive or the like (provided such an adhesive or the like is compatible with the method).

The device is suitably adapted to be mounted in a centrifuge to facilitate driving of the various media, reagents, buffers and the like through the matrix.

Alternatively the device is adapted to connect to one or more pumps to drive of the various media, reagents, buffers and the like through the matrix.

The device can suitably be a microfluidic device.

The device can be provided in association with a holder, e.g. a support which allows the device to be mounted in a centrifuge or other piece of laboratory equipment.

According to a third aspect, the present invention provides a system comprising a device according to the second aspect of the invention and associated sample handling apparatus.

The system may be adapted to perform several steps of the method of the present invention, e.g. at least the steps of protein precipitation, transfer of precipitate to the matrix and washing the matrix, and protease digestion.

Furthermore the system may additionally be adapted to perform one or more of cell lysis, protein extraction and elution of protein fragments from the matrix.

According to a fourth aspect, the present invention provides a kit comprising a device according to the second aspect of the invention and one or more containers comprising at least one of:
  a buffer medium for use in the device;
  reagents for cell lysis and solubilisation of membrane bound proteins;
  a protease;
  one or more washing/rinsing agents; and
  an elution agent.

Various suitable media, reagents and the like are discussed above.

The various features described and discussed in respect of the method of the first aspect of the invention are, of course, relevant to the device of the second aspect, the system of the third aspect and the kit of the fourth aspect.

Embodiments of the present invention will now be described, by way of non-limiting example, with reference to the accompanying drawings.

BRIEF DESCRIPTION OF THE FIGURES

FIG. 8. An example of the STrap processing device with a larger loading capacity—the STrap-tube unit. (a) The parts of the STrap-tube Spin-unit. (b) Assembled Spin-unit. (c) The STrap-tube with quartz/$C_{18}$ disk assembly. Five quartz and three $C_{18}$ disks are cut out of the corresponding membranes using 4.5 mm ID tubing. The disks are inserted/pressed down with a custom-made pusher into the 0.5 ml sample tube which was punctured with a 25 G needle in the bottom and lid parts.

SPECIFIC DESCRIPTION OF EMBODIMENTS OF THE INVENTION

A typical bottom-up proteomic experiment is based on tryptic proteolysis with subsequent characterization of the generated peptide products by mass spectrometry (MS)[1]. In order to obtain a thorough map of proteins, detergents (surfactants), amphipathic by nature, which facilitate solubilisation of hydrophobic proteins, are deployed. The conventional detergents are not compatible with mass spectrometry and must be eliminated from the samples prior to MS analysis. While attempts have been made to introduce mass spectrometry-friendly surfactants[2,3], such surfactants have not become widely accepted allegedly due to their high cost and suboptimal performance. Brought into the biochemistry spotlight in 1965[4], sodium dodecyl sulphate (SDS), an anionic surfactant, is the most widely used detergent for protein separation and solubilisation. The most common analytical utility of SDS is in separation of proteins by means of polyacrylamide gel electrophoresis (SDS-PAGE)[5]. The protein-containing gel bands may be cut out and in-gel digestion performed[6]. However, the overall value of such a procedure for proteome profiling and quantitation is limited due to such adverse effects as partial protein digestion, artifactual modifications, poor peptide recovery and the difficulties in processing of large numbers of gel bands if large-scale comparative profiling across multiple samples is needed. During recent years, the Filter Aided Sample Preparation Method (FASP) has gained popularity as one of the key tools for gel-free proteomic processing of the cellular and tissue SDS-extracted material[7]. The method, performed in ultrafiltration devices, is based on repetitive steps involving disruption of protein-SDS micelles by the chaotropic action of urea, removal of SDS and urea, and on-filter enzymatic cleavage of proteins which should result in adequate peptide yield and purity. The important analytical property of such a procedure is its unbiased nature, i.e. its ability to supply objective coverage of the hydrophobic (e.g. associated with membranes) and hydrophilic (e.g. cytoplasmic) cellular protein content. The FASP method, however, is very time-consuming, dependent on batch-to-batch reliable performance of the commercial spin-filter units, requires careful implementation and control to prevent drying-out or damage of the spin-filter membrane, and is disconnected from the clean-up step. The aim of the present invention work was to create a simple, efficient and reproducible 'workhorse' sample preparation tool, compatible with small sample amounts, which would combine the proven power of the SDS-based protein extraction with rapid detergent removal, protein digestion and in-situ clean-up of the peptides.

Figure 1:
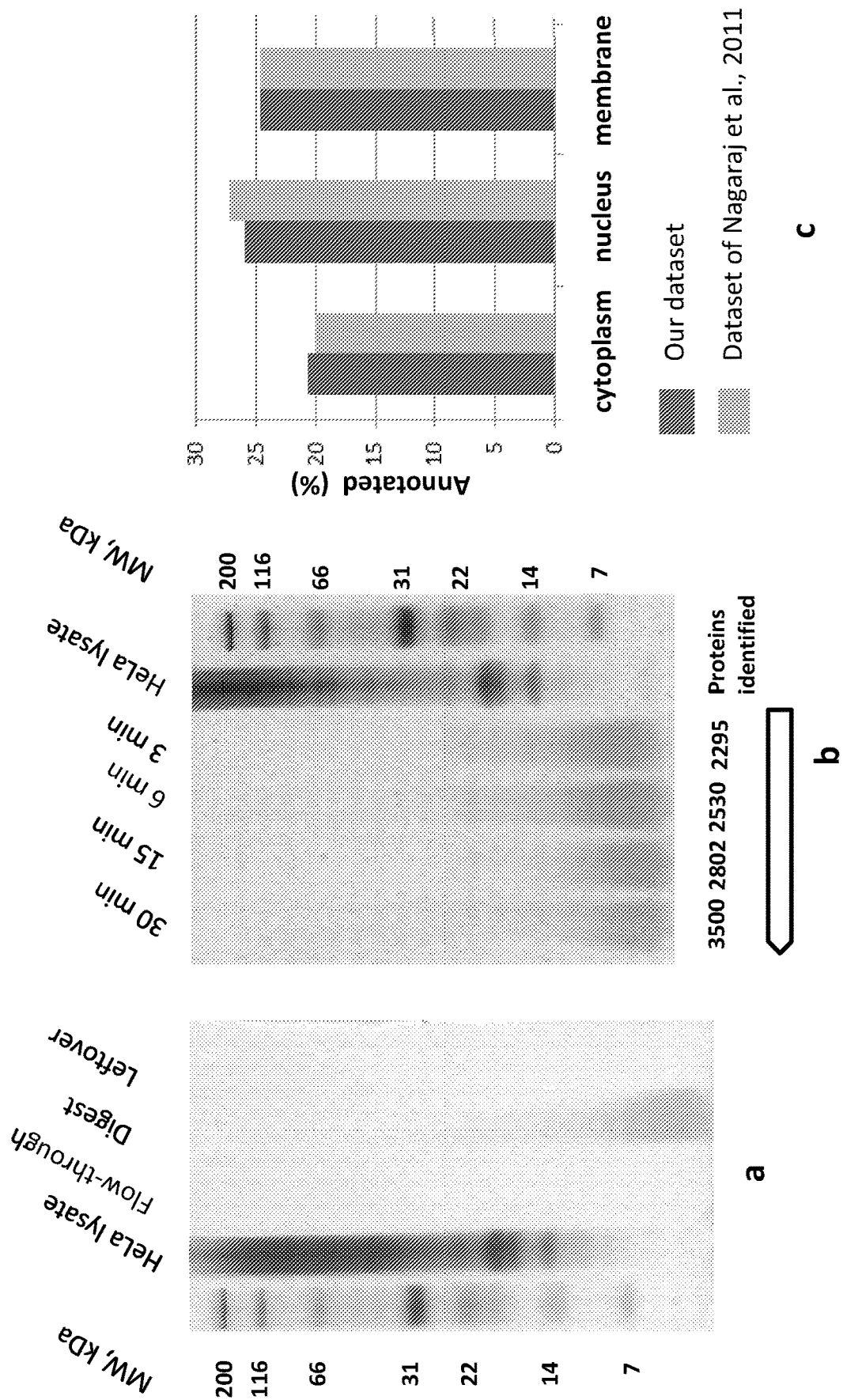
FIG. 1. Suspension Trapping (STrap)-based processing of HeLa SDS lysate. (a) The proteins are solubilised in the presence of high concentration of SDS, reduced and alkylated. The sample is acidified and introduced into the STrap tip (S-tip). The detergent and other contaminants are removed in the flow-through. The protein suspension is trapped in the S-tip and, after the introduction of trypsin, the digestion is performed for 30 min at 47° C. The key steps in the STrap processing are visualized with the use of the Coomasie-stained polyacrylamide gel. (b) The STrap method allows rapid reactor-type processing of the SDS-solubilised protein material. An average number of identified proteins from triplicate 240-min LC-MS/MS runs is shown. (c) Comparison of our HeLa proteome dataset obtained using RP-RP STrap processing with complete HeLa proteome by Nagaraj at al.[11]. The percentage of proteins with the appropriate Gene Ontology annotations is shown.
Figure 3:
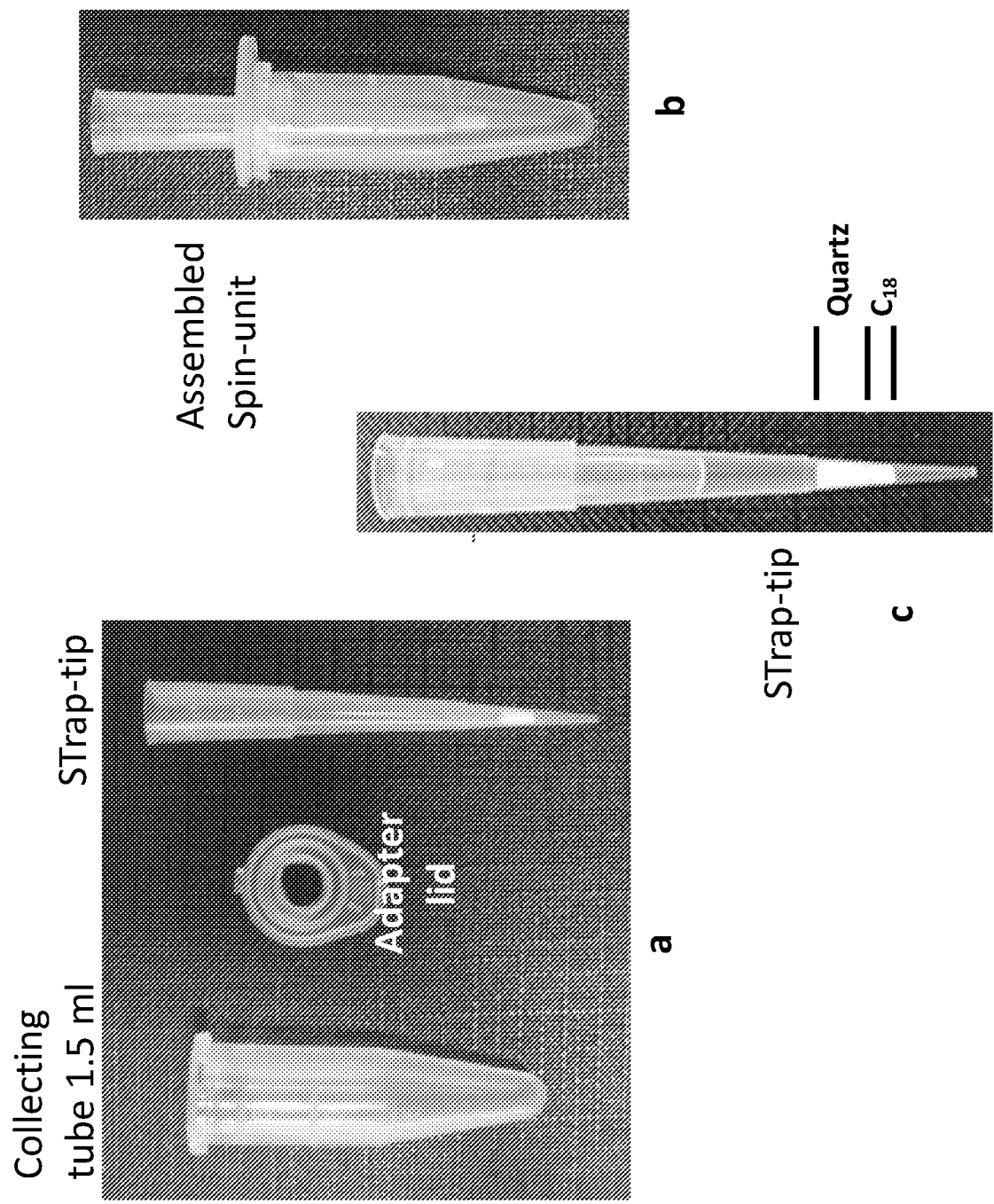
FIG. 3. STrap-tip processing unit. (a) The parts of the STrap-tip Spin-unit. (b) Assembled Spin-unit. (c) The STrap-tip with quartz/$C_{18}$ plugs stack.
Figure 4:
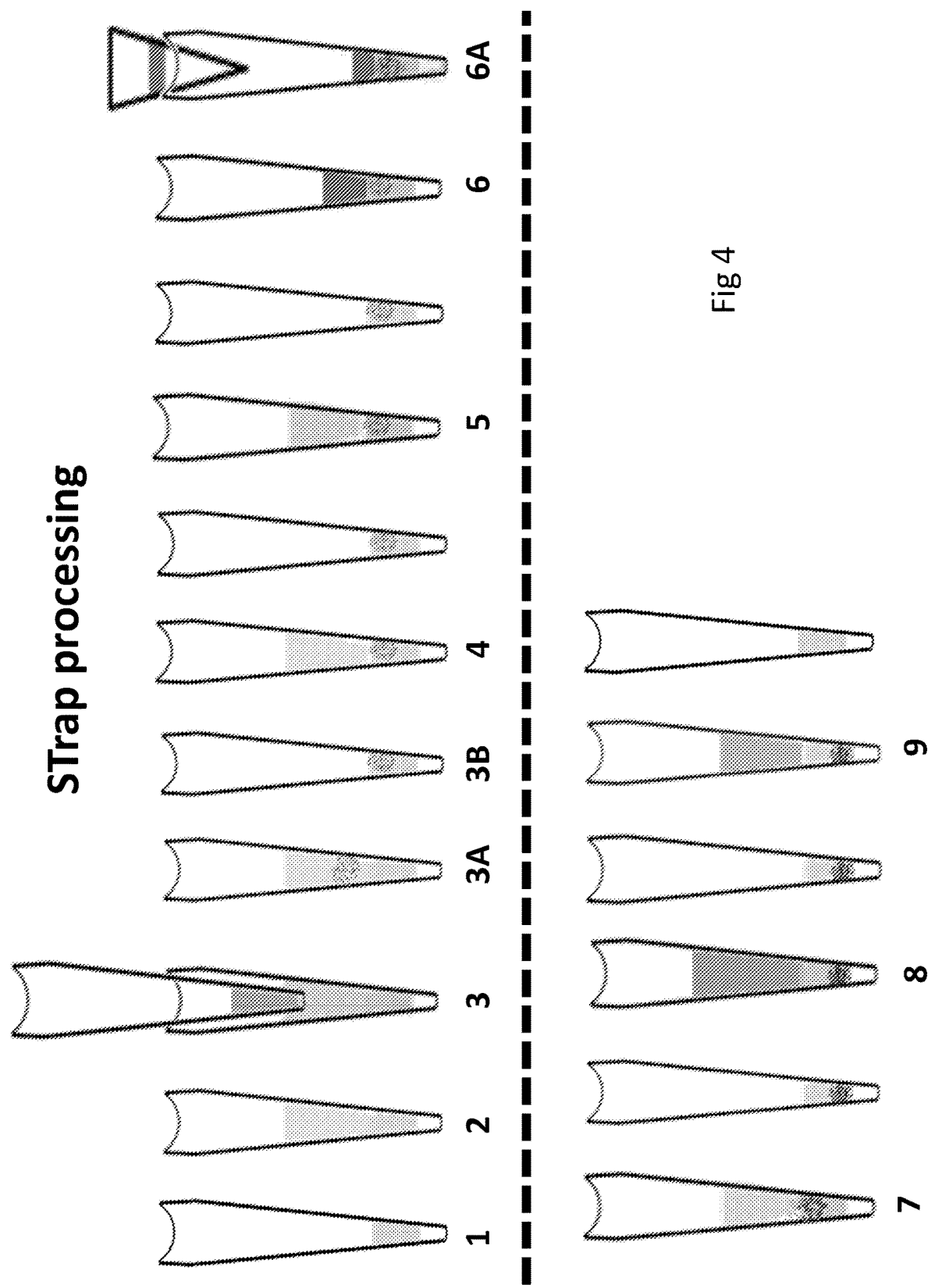
FIG. 4. Depiction of the STrap-tip-based sample processing. To the STrap-tip (1) the Strapping buffer is added (2), the acidified sample is added to the Strapping buffer (3) and the protein suspension is formed (3A). After the centrifugation, the protein suspension is trapped in the quartz stack (3B). Following the washes with the Strapping buffer (4) and water (5) an enzyme is added and the STrap tip is closed with a filter tip (6). After the incubation with an enzyme, the STrap tip is washed with the Ammonium Bicarbonate (AmBic) and TFA solutions (7, 8). The peptides, captured by the reversed phase plugs, are eluted with the Elution solution (9).

The key concept underpinning the basic STrap method design which we describe here is an instant creation of the fine protein particulate suspension, still susceptible to a protease action, from an SDS-solubilised protein solution, along with limiting the extent of the further aggregation of the suspension by its entrapment in the stack of an in-depth filtration material. This is achieved by adding the acidified protein-SDS mixture to a methanolic solution at a near-neutral pH in an S-tip incorporating depth filter and reversed phase membrane compartments (FIG. 3). The addition results in immediate creation of the fine protein suspension which is then captured by the depth filtration plugs. The SDS monomers which are soluble in the methanolic solution and other contaminants are washed away. The entrapped material is subsequently digested by an introduced protease. When the digestion is complete, the peptide products are transferred into and captured by the hydrophobic $C_{18}$ bottom part of the S-tip plug assembly, desalted, eluted and concentrated ready for the following liquid chromatography-tandem mass spectrometry (LC-MS/MS) run (FIG. 4). An example of the STrap tryptic processing of 30 μg protein from HeLa lysate is presented in FIG. 1a. Complete capture of the loaded protein material in the S-tip can be inferred from its evident absence in the flow-through fraction. After the 30-min incubation with trypsin at 47° C., the digest products are cleaned-up and eluted. No noticeable protein is left in the S-tip after the peptide elution step. In this case, approximately 3500 HeLa proteins are consistently identified in a 4-hour LC-MS/MS run injecting one third of the produced peptide amount. As the digestion happens in a limited volume and at elevated temperature, the tryptic enzymatic reaction is accelerated[8,9], with proteolysis being partially completed in only a few minutes allowing identification of more than two thousand proteins even after such a short time (FIG. 1b). By replacing the $C_{18}$ with $C_8$ plugs and in-tip reversed phase fractionation of the peptides into four fractions which were consequently analysed by LC-MS/MS, mimicking the two-dimensional reversed phase—reversed phase (RP-RP) chromatographic separation approach[10], we identified almost 5000 HeLa proteins in about 11 hours of total acquisition time. The overall representation of the characteristic protein groups (membrane, cytoplasmic and nuclear) in our data as indicated by Gene Ontology (GO) analysis was similar to that provided in the most complete exhaustive HeLa proteome data set of about 10,000 proteins obtained by extensive protein fractionation, FASP processing, and a total acquisition time of 288 hours[11] (FIG. 1c) confirming the unbiased output of our technique.

Figure 5:
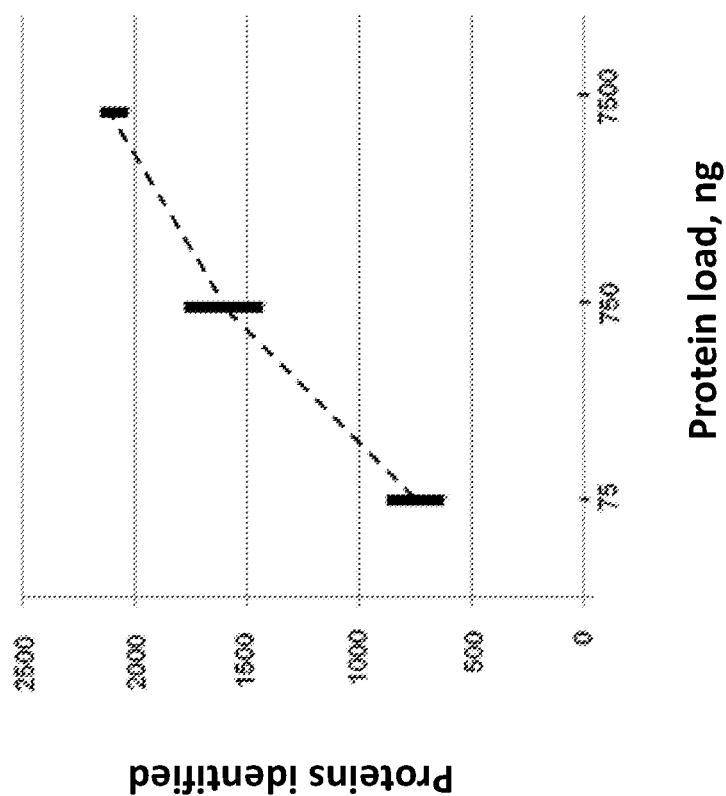
FIG. 5. STrap-tip processing of the sub-µg protein loads from HeLa SDS lysate. 120-min triplicate LC-MS/MS runs were used for protein identification.

To determine whether there are any unreasonable sample losses while working with sub-μg protein loads we processed amounts spanning the two orders of magnitude—75 ng, 750 ng and 7.5 μg of HeLa lysate. No disproportionate decrease in protein identifications was observed (FIG. 5), with 763, 1643 and 2096 average number of proteins identified, respectively, using 120-min triplicate LC-MS/MS runs, similar to the results reported for the FASP methodology[12].

Figure 2:
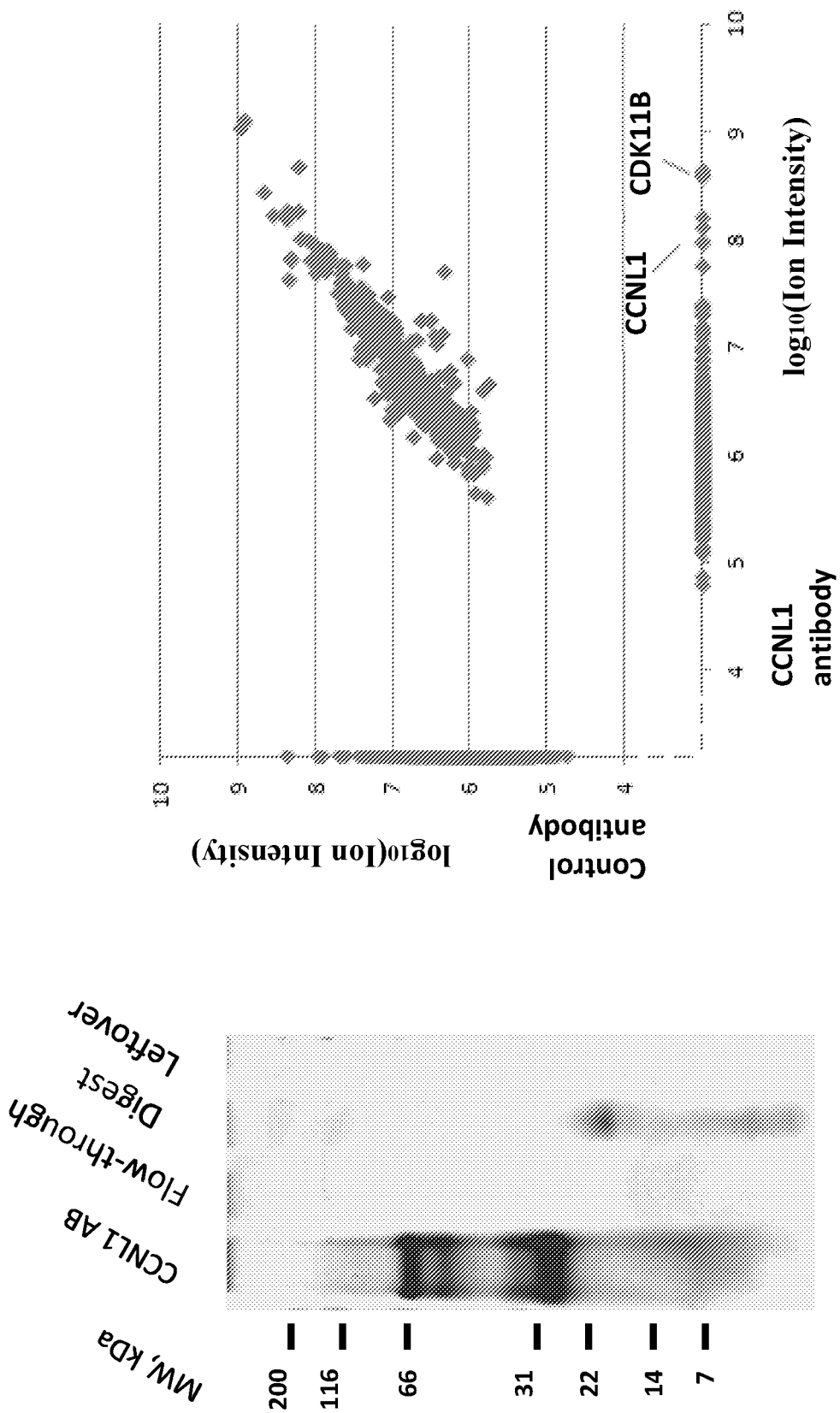
FIG. 2. Using STrap for immunoprecipitation (IP) profiling with low amounts of antibodies. (a) The IP was performed using 2 µg of anti-cyclin L1 (CCNL1) antibody, the eluate was processed with the STrap methodology. The key steps of the STrap processing are visualized with the use of the silver-stained polyacrylamide gel. (b) The eluted proteins from anti-CCNL1 and control antibody pull-down experiments were processed with the STrap methodology, identified and quantified by LC-MS/MS. The $\log_{10}$ values of the identified protein intensities are mapped onto the relevant axes.

In order to show the applicability of our method towards the analysis of less complex low protein amount samples, we performed an immunoprecipitation experiment using 2 μg of anti-cyclin L1 (CCNL1) polyclonal antibody which is directed against the N-terminal part of this transcriptional regulator thus leaving the C-terminal RS domain of CCNL1 accessible to interactions. The bound macromolecular complexes were eluted with 5% SDS and processed using the STrap methodology (FIG. 2a). As the result, in the pool of about 1000 identified proteins—background molecules and potential specific interactors—we could easily pinpoint, besides the targeted CCNL1, cyclin-dependent kinase 11B (CDK11B), the key CCNL1 target[13] (FIG. 2b), with 38% and 39% of the protein sequences covered, respectively. The experiment demonstrated that utilizing low amounts of antibodies and the STrap methodology could be efficiently used to uncover protein-protein interactions.

Figure 6:
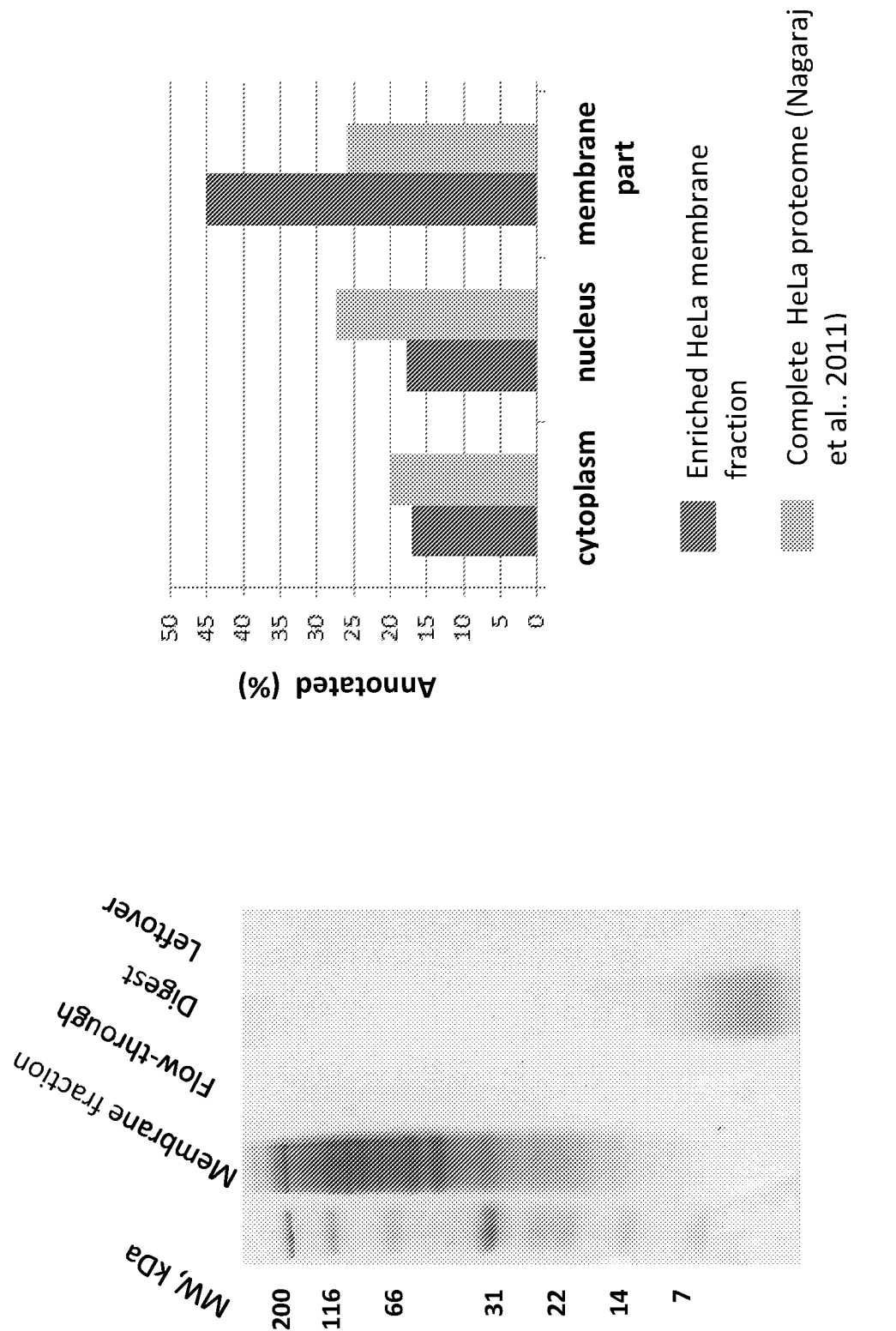
FIG. 6. STrap-tip processing of the enriched membrane protein fraction from HeLa cells. (a) The key steps in the STrap processing are visualized with the use of the Coomasie-stained polyacrylamide gel. (b) Comparison of the obtained enriched membrane protein dataset with the complete HeLa proteome by Nagaraj at al.[11] The percentage of proteins with the relevant Gene Ontology annotations is shown.

One of the most important characteristics of any bottom-up proteomics sample preparation method is its ability to process membrane proteins which due to their inherent hydrophobicity are not easily enzymatically cleaved in aqueous environments. We used a modified procedure of Bordier[14] for preparation of an enriched fraction of membrane proteins from HeLa cells. The procedure is based on the ability of a solution of the non-ionic detergent Triton X-114 to extract protein material at cold temperatures with subsequent separation at temperatures exceeding 20° C. into an aqueous phase, containing hydrophilic proteins, and detergent phase, containing membrane proteins. The obtained enriched fraction of membrane proteins together with Triton X-114 detergent was then solubilised with 15% basic SDS solution—this solubilisation step made it possible to flawlessly process the sample by the STrap protocol using tryptic digestion for one hour at 47° C. (FIG. 6a). As the result, more than 3000 proteins were identified with 45% of the proteins being categorized by GO annotation as being part of a membrane as compared with only 25% in the whole HeLa proteome (FIG. 6b). The experiment also demonstrates the STrap capability to process samples with high SDS content.

Figure 7:
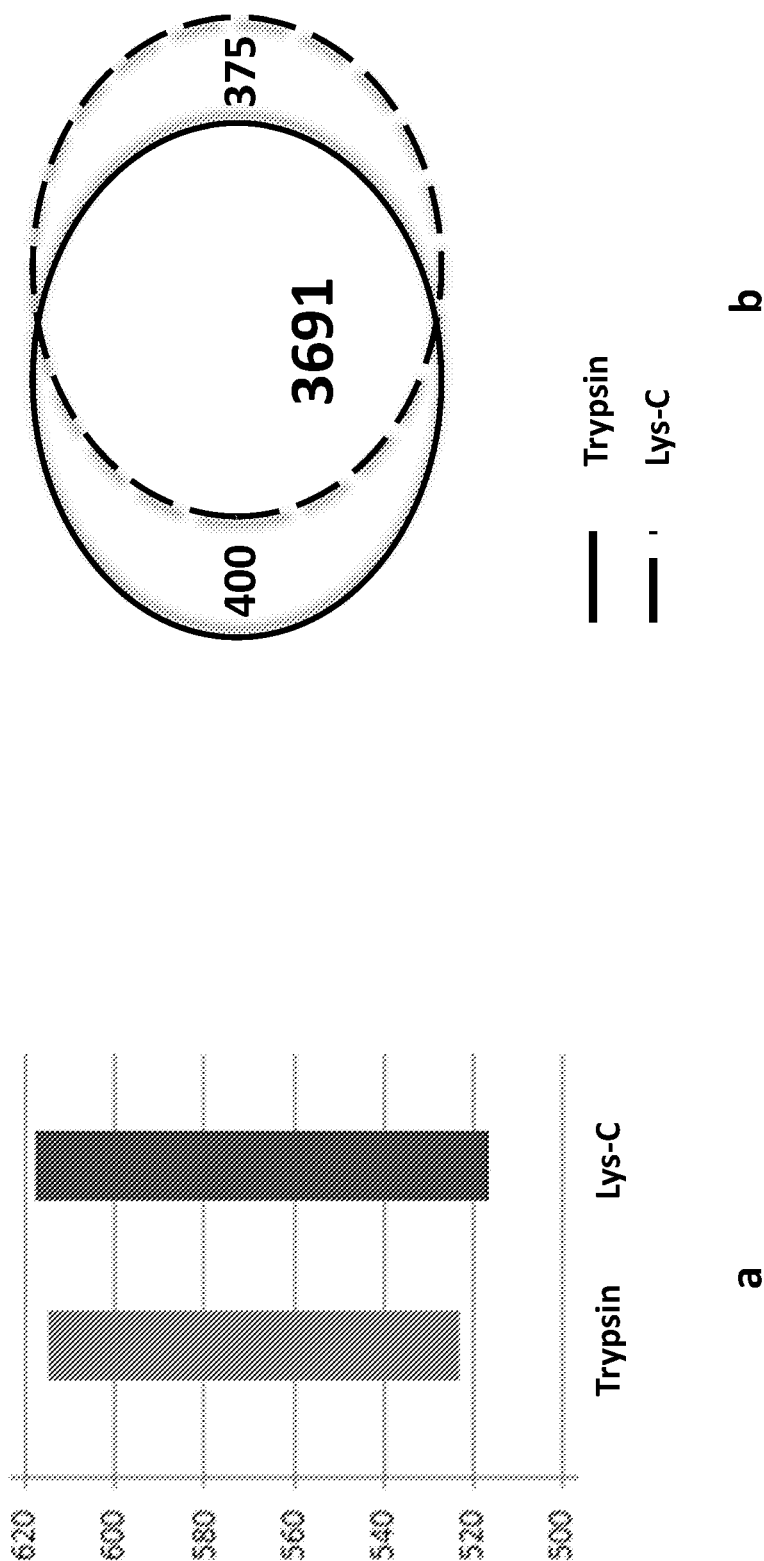
FIG. 7. STrap-tip processing of the HeLa lysate using Lys-C protease (Wako). (a) The use of Lys-C protease identifies comparable to the tryptic processing protein numbers (based on triplicate 240-min LC-MS/MS runs). (b) Venn diagram shows the overlap between the proteins identified with trypsin and Lys-C proteases.

Even though our method was originally optimized using trypsin as the most common robust protease with high primary specificity and thermal stability, we reasoned that deployment of the STrap concept could also be helpful while working with additional enzymes. However, the other enzymes such as Lys-C, for example, perform best at the manufacturer's recommended temperature conditions. Nonetheless, besides more lengthy incubation period with an enzyme, the core of the STrap procedure remains unaltered and the advantage of the overall improvement in sample preparation times is retained. To demonstrate the idea's applicability, we performed the STrap procedure using 30 µg of HeLa lysate and Lys-C endoproteinase with 4-hour incubation at 37° C. in a humidified chamber. The Lys-C performance in terms of a number of protein identifications was similar to that of trypsin—more than 3500 proteins were routinely identified using 240-min LC-MS/MS runs injecting one third of the resultant peptides amount (FIG. 7a) and about 4000 proteins were identified using the data from three replicate runs (FIG. 7b).

In the described STrap-tip format, our method provides the means for rapid processing of the SDS-solubilised protein material from about 50 µg down to sub-microgram amounts. Taking into account the fact that the constantly evolving modern LC-MS/MS systems with high sensitivity, accuracy and sequencing speed require only several micrograms of peptides for comprehensive proteomics profiling[15, 16], the tip implementation of the STrap method is going to be sufficient for many a routine proteomics task. If necessary, however, larger protein quantities may be processed by adhering to the explained STrap principles and designing appropriate in-depth trapping/processing units with an increased surface area. An example of the larger capacity unit—STrap-tube—is presented in FIG. 8. This work outlines the concept and demonstrates the practical applicability of the Suspension Trapping (STrap) methodology facilitating proteomics analysis of the various SDS-solubilised protein mixtures—cellular lysates, membrane preparations and immunoprecipitates. Importantly, our method provides rapid, unproblematic, reproducible and simple sample processing capability for the low microgram protein quantities—the 'precarious' area working in which formerly required, in addition to technical dexterity, considerable inputs of time and endeavour.

Methods

The S-Tip Design

Figures 9, 10:
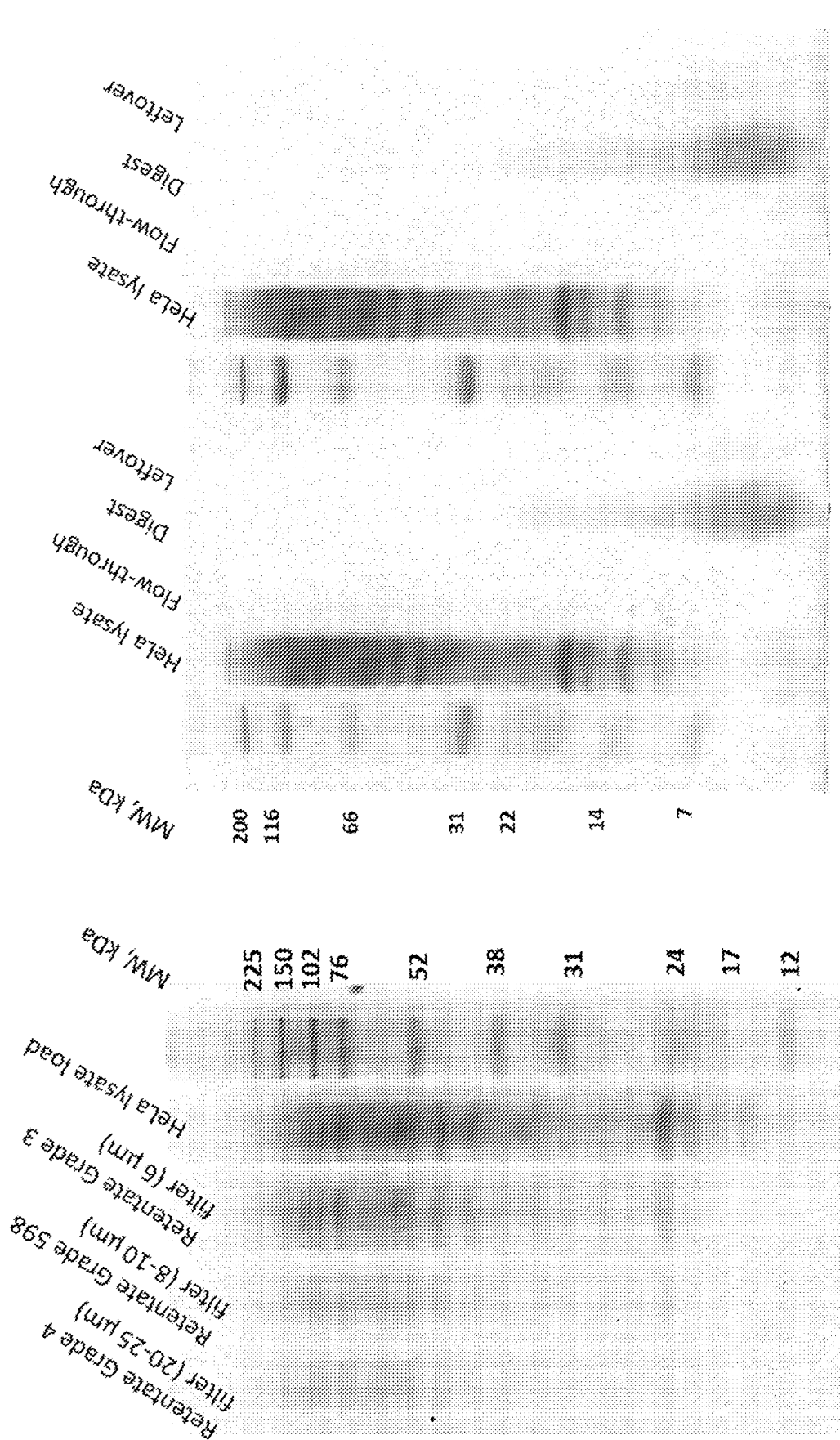
FIG. 9. Estimation of the particle size range formed during the STrap processing. HeLa SDS lysate was acidified and precipitated in the neutral methanolic solution and passed through the filter paper stacked in a pipette tip. The trapped protein material was eluted with 2× sample loading buffer and visualized with the use of the Coomasie-stained polyacrylamide gel. EEs FIG. 10. Comparison of borosilicate glass (GF/D) filter with quartz (MK360) filter performance for the STrap processing of cellular lysates. The key steps are visualized with the use of the Coomasie-stained polyacrylamide gel.

The basic trapping and clean-up S-tip device is made either from the quartz fibre (MK360, Munktell or QM-A, Whatman) filters, borosilicate glass fibre (GF/D, Whatman) filter or their combination and reversed phase membrane (Empore $C_{18}$, 3M) disk plugs stacked together in a pipette tip (D200, Gilson) using gauge 14 blunt end needle (Z261394, Sigma). Eleven MK360 quartz plugs or nine borosilicate GF/D glass plugs or combination of either six borosilicate GF/D glass and five quartz MK360 plugs or six QM-A quartz and five MK360 quartz plugs, and three or four $C_{18}$ plugs are forced into the 200 µl pipette tip end with the aid of a pusher—the piece of 1/16" OD PEEK tubing (1535, Upchurch Scientific). In order to compact the plugs and make them adhere to each other, the stack is further pressed down and compressed with a piece of the PEEK tubing several times. Originally, the quartz fibre filter from Munktell (MK 360) was chosen as a preferred in-depth filtration material because of its pure quartz composition, ability to trap particles down to sub-micron range, absence of binders and heat pre-treatment which provide an adequate near-contaminant-free trapping matrix environment. However, the borosilicate glass binderless fibre filter from Whatman (GF/D) also proved to work well for the described applications. FIG. 10 shows a comparison of the results of using MK360 and GF/D filters in the standard STrap protocol as visualised by Coomasie-stained polyacrylamide gel electrophoresis. Even though the borosilicate glass fibre displays a somewhat stronger peptide binding in comparison to the quartz material, the use of GF/D filter with larger pore sizes and loading capacity may be beneficial when working with the protein loads exceeding 30 µg. Alternatively, the quartz QM-A (Whatman) filter with larger than MK360 material pore sizes could be utilized. The underlying Empore reversed phase material gives mechanical support for the upper plugs, captures stray particles as well as a shed fibre material, and, in addition, serves as a medium for the final clean-up of the peptides.

Cell Solubilisation and Lysate Processing

A HeLa cell pellet (8 million cells) was lysed in excess of a lysis solution (5% SDS in 50 mM TRIS-HCl, pH 7.6) at room temperature (RT). To shear the DNA, the sample was sonicated briefly with a probe sonicator. Then, dithiothreitol (DTT) (stock solution of 1M in $H_2O$) was added to a final concentration of 20 mM. The extract was heated at 95° C. for 5 min and then clarified by centrifugation at 12,100×g for 10 min. Protein concentration was measured by tryptophan fluorescence as described previously[15]. Iodoacetamide (IAA) (stock solution of 0.9 M in $H_2O$) was added to a final concentration of 150 mM. Following incubation for 15 min in the dark, the lysate was ready for further processing by the STrap method.

Basic Sample Processing Procedure by Strap Method

The required protein amounts (75 ng-30 µg), in triplicates, were prepared by appropriate dilutions of the alkylated SDS HeLa lysate with the lysis solution to a final volume of 18 µL and processed adhering to the STrap protocol (see Exemplary Suspension Trapping Methodology) using 30-min tryptic digestion at 47° C. performed in the O-tubes pre-heated to 47° C.

Mass Spectrometry and Data Analysis

Peptides were separated online by reversed-phase capillary liquid chromatography (LC) using RSLCnano system (Dionex) connected to a 40-cm capillary emitter column made in-house (inner diameter 75 µm, packed with 3 µm Aqua $C_{18}$ media). The chromatography system was hyphenated with a linear quadrupole ion trap-orbitrap (LTQ-Orbitrap) Velos mass spectrometer (Thermo). The total acquisition times used for basic STrap processing were either 120, 200 or 240 min, the major part of the chromatographic gradient was 2%-32% acetonitrile (ACN) in 0.2% formic acid. Survey MS scans (scan range of 300-1500 amu) were acquired in the orbitrap with the resolution set to 60 000. Up to 20 most intense ions per scan were fragmented and analysed in the linear trap. Data were processed against a Uniprot human protein sequence database (October, 2012) with MaxQuant 1.3.0.5 software[17] and Andromeda search engine[18]. The mass tolerance for MS scan was set to 7 ppm, the fragment mass tolerance for MS/MS was set to 0.5 Th. Carbamidomethylation of cysteine was set as a fixed modification, with protein N-terminal acetylation and oxidation of methionine as variable modifications, two missed cleavages, and at least 1 unique peptide for valid protein identification. The maximum protein and peptide false discovery rates were set to 0.01. Bioinformatics analysis of Gene Ontology (GO) features was undertaken with Perseus 1.3.0.4 (www.maxquant.org).

Preparation of the Enriched Membrane Protein Fraction with Triton X-114

To a HeLa cell pellet containing 8 million cells, 500 µL of 1% Triton X-114 ice-cold solution in phosphate-buffered saline (PBS) pH 7.4 was added. The sample was rotated in the cold room for 10 min and centrifuged at 5000×g for 10 min at 5° C. The supernatant, containing mostly membrane and cytoplasmic proteins, was removed, placed at 45° C. for 10 min, and then centrifuged at 12,100×g for 10 min at RT. The upper fraction was removed. The protein pellet and the Triton X-114 lower fraction were washed once by reconstitution in 300 µL of PBS preheated to 45° C. and centrifugation at 12,100×g for 7 min at RT. The upper fraction was removed and the lower fraction and the pellet were solubilised with 200 µL of 15% SDS in 50 mM TRIS-HCl, pH 7.6. DTT was added to a final concentration of 20 mM and the sample was heated at 95° C. for 5 min. The solution was clarified by centrifugation at 12,100×g for 10 min (as Triton X-114 interferes with tryptophan fluorescence measurement, for estimation of protein concentration by this method proteins in a sample aliquot were precipitated and recovered into 5% SDS 50 mM TRIS-HCl, pH 7.6 buffer). 25-µg protein aliquots were taken and IAA added to a final concentration of 150 mM. Following incubation for 15 min in the dark, the samples were ready for further processing by the quartz-based STrap method using a tryptic incubation for one hour at 47° C. The peptides were analysed by the 240-min LC-MS/MS method.

Immunoprecipitation

Immunoprecipitation using polyclonal rabbit anti-cyclin L1 (anti-CCNL1) antibody (A302-058A, Bethyl Laboratories) and control IgG from rabbit serum (15006, Sigma) was performed as outlined below. HeLa cell pellet (25 million cells) was extracted with 1.0 ml of Radio-Immunoprecipitation Assay (RIPA) buffer containing protease inhibitors (Complete™ Mini Protease Inhibitor Cocktail Tablet, EDTA-free, Roche). The extract was cleared by centrifugation at 12,100×g for 10 min. A 2 µg aliquot of antibody was added to the extract. The mixture was rotated at RT for 30 min. Afterwards, 30 µl of Protein G magnetic beads (Dynabeads, Life Technologies) was added and the mixture was rotated for another 30 min. After removal of the extract and a wash with RIPA buffer, bound proteins were eluted by incubating the beads with 30 µl of 5% SDS 50 mM TRIS-HCl, pH 7.6 buffer containing 20 mM DTT at 90° C. for 5 min. Alkylation was performed by adding IAA to the final concentration of 150 mM. After processing by the quartz-based STrap method, the resultant peptides were analysed by LC-MS/MS using the 200-min acquisition method.

Reversed Phase Sample Fractionation with STrap

The modified quartz-based STrap tip was created by substituting the $C_{18}$ with $C_8$ reversed phase material. 50 µg of HeLa lysate was introduced into the STrap tip, digested with trypsin at 47° C. for 30 min using the O-tubes preheated to 47° C. and the peptides were transferred to the reversed phase plug compartment according to the basic STrap protocol. Afterwards, four peptide fractions were obtained by consecutive elutions with 50 µl of 5% ACN in water, 10% ACN in water, 15% ACN in water and 60% acetonitrile in 0.5% formic acid (FA). The concentrated peptide fractions were chromatographically separated online with the following 140 min gradients—2-15% ACN in 0.2% FA, 2-21% ACN in 0.2% FA, 9-25% ACN in 0.2% FA, 12-36% ACN in 0.2% FA, respectively, and analysed by MS/MS similarly to the described above.

Lysyl Endopeptidase (Lys-C) and STrap

The samples, 30 µg of HeLa lysate, were processed similarly to the quartz-based STrap protocol except that, instead of trypsin, Lys-C protease (125-05061, Wako) was used (0.033 µg/µl in Tris-HCl pH 9.0 buffer) and the incubation was performed for 4 hours at 37° C. in a humidified chamber. The resultant peptides were analysed by LC-MS/MS using the 240-min acquisition method as described above.

Exemplary Suspension Trapping Methodology (STrap)

Tryptic Digest, Maximum Load of 50 µg of Total Protein

1. Materials

Solutions and Reagents

Milli-Q water ($H_2O$)

AmBic (Ammonium Bicarbonate) solution: 50 mM $NH_4HCO_3$ in $H_2O$

Lysis buffer: 5% (w/v) sodium dodecyl sulfate (SDS), 50 mM Tris/HCl pH 7.6

STrapping buffer: 90% methanol, 100 mM Tris/HCl pH 7.1

Phosphoric acid stock solution: 12.15% in $H_2O$

DTT stock solution: 1 M dithiothreitol in $H_2O$, prepared on the day of experiment IAA stock solution: 0.9 M iodoacetamide in $H_2O$, prepared on the day of experiment Trypsin solution: 0.033 µg/µl of trypsin (03708985001, Roche or V5111, Promega) in 50 mM NH4HCO3, prepared prior to starting the STrap processing step and kept on ice TFA solution 1: 0.5% trifluoroacetic acid in $H_2O$ TFA solution 2: 10% trifluoroacetic acid in $H_2O$ Elution solution: 70% acetonitrile, 0.5% formic acid in $H_2O$ FA solution: 0.2% formic acid in $H_2O$ Equipment Bench-top centrifuge (for example MiniSpin, Eppendorf)

Probe Sonicator (for example Soniprep 150, MSE)

Heating block suitable for handling 1.5 ml microtubes (for example PHMT, Grant Bio)

Plastic Syringe, 20 ml (for example 301031, BD) with a custom adapter to fit into 200 µl pipette tips Vacuum Concentrator (for example SpeedVac, Thermo)

STrap-tip (S-tip): S-tip is made either from the quartz fibre (MK360, Munktell or QM-A, Whatman) filters, borosilicate glass fibre (GF/D, Whatman) filter or their combination and reversed phase membrane (Empore $C_{18}$, 3M) disk plugs stacked together in a pipette tip (D200, Gilson) using gauge 14 blunt end needle (Z261394, Sigma). Eleven MK360 quartz plugs or nine borosilicate GF/D glass plugs or combination of either six borosilicate GF/D glass and five quartz MK360 plugs or six QM-A quartz and five MK360 quartz plugs, and three or four $C_{18}$ plugs are forced into the 200 µl pipette tip end with the aid of a pusher—the piece of 1/16" OD PEEK tubing (1535, Upchurch Scientific). In order to make the plugs adhere to each other, the stack is further pressed down and compacted with a piece of the 1/16" OD PEEK tubing several times.

O-tube: A 1.5 mL microcentrifuge tube (72.690.001, Sarstedt) with an opening punctured in the tube's lid (alternatively, a pipette tip lid-adapter for microcentrifuge tubes could be used). The S-tip and O-tube comprise the Spin-unit.

Filter tips, 10 µl (TF-300-R-S, Axygen).

2. Methods 2.1 Cell Lysis and Reduction of Cysteine Residues

Cells are lysed in excess of the Lysis buffer (ca. 1:8-1:10 sample-to-Lysis buffer volume ratios) at room temperature. To shear the DNA, the lysate is shortly sonicated using a probe sonicator. DTT stock solution is added to a final concentration of 20 mM. The extract is heated up at 95° C. for 5 min. The extract is clarified by centrifugation at 12,100×g for 10 min. Protein concentration could be measured by tryptophan fluorescence (Wisniewski, J. R., Dus, K. & Mann, M. *Proteomics Clin Appl* 2013).

Notes:

Temperatures below 15° C. cause SDS precipitation and thus must be avoided during the sample processing steps. The lysate could be aliquoted and stored at −20° C. and, when needed, processed further after heating it up for 2 min at 95° C.

2.2 Alkylation of Cysteine Residues

IAA stock solution is added to a final concentration of 150 mM with the incubation step being at least 15 min in a dark.

2.3 Preparation of the Trypsin Solution

Trypsin solution (0.033 µg/µl in 50 mM $NH_4HCO_3$) is prepared prior to the step 2.4 and placed on ice.

2.4 Sample Processing by STrap (Tryptic Digest and Peptide Desalting)

1. Pre-heat the heating block to 47° C.
2. Insert the S-tip into the O-tube.
3. (See Notes) Add 120 µl of the STrapping buffer into the S-tip onto the top of the quartz stack. Wait for 1 min.
4. (See Notes) To 18 µl of the sample add 2 µl of the Phosphoric acid stock solution. Mix by pipetting up and down.
5. Slowly add the acidified sample into the upper quarter of the STrapping buffer in the S-tip. Insert the S-tip into the O-tube. Place the Spin-unit into the centrifuge and mark the S-tip part facing outwards.
6. (See Notes) Centrifuge the Spin-unit at 2800×g for 2 min.
7. Dispose of the tube with the flow-through.
8. Add 70 µl of the STrapping buffer into S-tip. Insert the S-tip into the fresh O-tube. Place the Spin-unit into the centrifuge with the S-tip mark facing inwards. Centrifuge the Spin-unit for 45 sec at 2800×g.
9. Add 30 µl of the AmBic solution into S-tip and centrifuge the Spin-unit for 30 sec at 2800×g.
10. Add 22 µL of the Trypsin solution into the S-tip onto the top of the plugs stack. Push down the solution using the syringe with a customized tip adapter till the solution meniscus is positioned ca. 3 mm above the top of the plugs stack.
11. Close the top of the S-tip with the 10 µl filter tip.
12. Insert the closed S-tip into the fresh O-tube, place the unit into the heating block at 47° C. and cover with the aluminium foil.
13. (See Notes) Incubate for 60 min.
14. Remove the Spin-unit from the heating device. Take out the filter tip. Add 50 µl of the AmBic solution into the S-tip onto the top of the plugs stack. Wait 30 sec.
15. Centrifuge the Spin-unit at 2300×g for 60 sec.
16. (Optional) Remove the S-tip from the O-tube. Add 3 µl of the TFA solution 2 to the flow-through. Load the acidified flow-through into the S-tip. Insert the S-tip back into the O-tube. Centrifuge the Spin-unit at 2300×g for 60 sec.
16. Add 100 µl of the TFA solution 1 into the S-tip. Centrifuge the Spin-unit at 2500×g for 90 sec.
17. Place the S-tip into the fresh O-tube. Add 80 µL of the Elution solution into the S-tip, centrifuge the Spin-unit for 5 sec at 2500×g, wait 30 sec and then centrifuge the Spin-unit for 1.0 min at 2500×g.
18. (Optional) Add 50 µl of the Elution solution into the S-tip, centrifuge the Spin-unit for 60 sec at 2500×g.
19. The eluate in the O-tube, containing desalted peptides, is concentrated in the SpeedVac to the final volume of 5-12 µL. If needed, the concentrated peptide mixture could be diluted with the FA solution up to the required volume. To remove any particulate matter, spin down the peptide samples before loading them into the autosampler vials or plates.

Notes:

1. After each centrifugation step make sure that all added solution has gone through the S-tip.
2. A properly assembled S-tip can tolerate the centrifugal acceleration of at least 4000×g.
3. The typical working ratio between the STrapping buffer in the S-tip (step 3) and the acidified sample (step 4) is 6:1 (acceptable tested ranges 4.5:1 to 7:1), e.g. the STrapping buffer 120 µl and the added acidified sample 20 µl.
4. In step 4, the sample could be diluted with the Lysis buffer up to the required volume before the acidification.
5. The final concentration of the phosphoric acid in the sample (step 4) is 1.2% which is achieved by addition of the phosphoric acid stock solution to the sample at 1:10 ratio.
6. Alternatively to the high-temperature (47° C.) digestion, digestion for 3-4 hours at 37° C. in a humidified chamber could be performed.

Cys-STrap Method

The following method is an adaptation of the method described above, where the surface of the matrix is modified to increase the affinity of the surface of the matrix for cysteine residues of protein/protein fragments specifically, thereby allowing those proteins/protein fragments that comprise cysteine residues to be analysed separately to those proteins/protein fragments that do not comprise cysteine residues.

Tryptic Digest with Enrichment of the Cysteine Containing Peptides, Maximum Protein Load 60 µg 1. Materials Solutions and Reagents Milli-Q Water ($H_2O$)

Methanol

AmBic (Ammonium Bicarbonate) solution: 40 mM $NH_4HCO_3$ in $H_2O$

AmBic-ACN solution: 20% acetonitrile in 40 mM $NH_4HCO_3$

Lysis buffer: 5% (w/v) sodium dodecyl sulfate (SDS), 50 mM Tris/HCl pH 7.5

STrapping buffer: 90% methanol, 100 mM Tris/HCl pH 7.1

Phosphoric acid solution: 12.15% in $H_2O$

DTT solution: 1 M dithiothreitol (DTT) in $H_2O$, freshly prepared

DTT elution solution: 50 mM DTT, 5% acetonitrile, 40 mM $NH_4HCO_3$, freshly prepared IAA solution: 1 M iodoacetamide in $H_2O$, freshly prepared Trypsin solution: 0.1 µg/µl of trypsin (V5111, Promega) in 40 mM NH4HCO3, prepared prior to starting the Cys-STrap processing step and placed on ice FA solution 1: 2% formic acid in $H_2O$
FA solution 2: 50% acetonitrile, 0.5% formic acid in $H_2O$
FA solution 3: 10% formic acid
Isopropanol solution: 50% isopropanol in $H_2O$
Equipment
Bench-top centrifuge (for example MiniSpin, Eppendorf)
Probe sonicator (for example Soniprep 150, MSE)
Heating block suitable for handling 1.5 ml microtubes (for example PHMT, Grant Bio)
Plastic syringe, 20 ml (for example 301031, BD) with a custom adapter to fit into 200 µl pipette tips
Vacuum concentrator (for example SpeedVac, Thermo)
Cys-STrap Tip
MK360 quartz filter is modified with pyridyldithiol, i.e. MK360-50 mm filter is incubated with 10 ml of 2% (3-Aminopropyl)triethoxysilane (APTES) solution in acetone for 20 min and then washed several times with acetone. 5 mg of N-succinimidyl 3-(2-pyridyldithiol)propionate (SPDP) is dissolved in 0.4 ml of dimethyl sulfoxide (DMSO) and added into 9.6 ml of phosphate buffered saline (PBS) (pH 7.4, 15 mM EDTA). The aminopropyl-modified filter is incubated with the resultant SPDP solution for 2 hours at room temperature and then washed several times with the PBS/15 mM EDTA solution and air dried overnight.

Using a 14 gauge blunt needle, the Cys-STrap tip is constructed by inserting 12 plugs of the pyridyldithiol modified MK360 material into a 200 µl pipette tip—similarly to the original STrap tip protocol however no underlying $C_{18}$ membrane compartment is added in this case.

O-tube: A 1.5 mL microcentrifuge tube (72.690.001, Sarstedt) with an opening punctured in the tube's lid (alternatively, a pipette tip lid-adapter for microcentrifuge tubes could be used). The Cys-STrap tip and O-tube comprise the Spin-unit Filter tips, 10 µl (TF-300-R-S, Axygen)
2. Methods
2.1 Cell Lysis and Reduction of Cysteine Residues Cells are lysed in excess of the Lysis buffer (ca. 1:10 sample-to-Lysis buffer volume ratios) at room temperature. To shear the DNA, the lysate is shortly sonicated using a probe sonicator. DTT solution is added to the final concentration of 20 mM. The extract is heated up at 95° C. for 5 min. The extract is clarified by centrifugation at −12,000×g for 10 min.

2.2 Preparation of the Trypsin Solution

Trypsin solution (0.1 µg/µl in 40 mM NH4HCO3) is prepared prior to the step 2.3 and placed on ice.
2.3 Sample Processing by Cys-STrap
1. Pre-heat the heating block to 47° C.
2. (See Notes) Add 120 µl of the STrapping buffer into the Cys-STrap tip onto the top of the quartz stack. Wait for 1 min.
3. (See Notes) To 18 µl of the sample add 2 µl of the Phosphoric acid stock solution. Mix by pipetting up and down.
4. Slowly add the acidified sample into the upper quarter of the STrapping buffer in the Cys-STrap tip. Insert the Cys-STrap tip into the O-tube. Place the Spin-unit into the centrifuge and mark the Cys-STrap tip part facing outwards.
5. Centrifuge the Spin-unit at 2500×g for 1 min.
6. Dispose of the tube with the flow-through.
7. Add 70 µl of the STrapping buffer into Cys-STrap tip. Insert the S-tip into the fresh O-tube. Place the Spin-unit into the centrifuge with the Cys-STrap tip mark facing inwards. Centrifuge the Spin-unit for 45 sec at 2500×g.
8. Add 40 µl of the Am Bic solution into Cys-STrap tip and centrifuge the Spin-unit for 30 sec at 2500×g.
9. Add 35 µL of the Trypsin solution into the Cys-STrap tip onto the top of the plug stack. Push down the solution using the syringe with a customized tip adapter till the solution meniscus is positioned ca. 4 mm above the top of the plug stack.
10. Close the top of the Cys-STrap tip with the 10 µl filter tip.
11. Insert the closed Cys-STrap tip into the fresh O-tube, place the unit into the heating block at 47° C. and cover with the aluminium foil. Incubate for 60 min.
12. Remove the Spin-unit from the heating device. Take out the filter tip. Add 40 µl of the AmBic solution into the Cys-STrap tip onto the top of the plug stack.
13. Centrifuge the Spin-unit at 2000×g for 30 sec.
14. Add 50 µl of the Ambic-ACN solution into the Cys-STrap tip onto the top of the plug stack.
Centrifuge the Spin-unit at 2000×g for 30 sec.
15. Collect the flow-through fraction. The peptides in this fraction could be either fractionated by ion-exchange (e.g. SAX STAGE tip fractionation[1]) or cleaned by the basic $C_{18}$ STAGE tip[2] method after having evaporated acetonitrile.
16. Cys-STrap tip is washed consecutively with 100 µl of the FA solution 1, FA solution 2, isopropanol solution, and Ambic-ACN solution using centrifugation in the Spin-unit and decanting the flow-through when necessary.
17. Cys-STrap tip is washed with 50 µl of methanol solution using centrifugation in the Spin-unit.
18. 40 µl of DTT elution solution is added into the Cys-STrap tip. The tip is placed into a fresh tube, the DTT elution solution is pushed down with the syringe-adapter till the solution meniscus is positioned ca. 5 mm above the top of the plug stack. Incubation is performed at 37° C. for 45 min.
19. 30 µl of the Ambic solution is added into the Cys-STrap tip and pushed down with the syringe-adapter.
20. 50 µl of the Ambic-ACN solution is added into the Cys-STrap tip and pushed down with the syringe-adapter.
21. 20 µl of the IAA solution is added to the eluate and the mixture is incubated in the dark for 30 min.
22. The mixture is acidified by the FA solution 3 to the final concentration of 0.5% formic acid.
23. Following the above alkylation step, the peptides could be cleaned up by the SCX tip extraction[2] (e.g. the peptides could be loaded onto the SCX STAGE tip pre-activated with the consecutive washes of methanol and 20% acetonitrile in 0.5% formic acid, washed with 20% acetonitrile in 0.5% formic acid, eluted with 0.7 M Ammonium Acetate in 20% acetonitrile, dried down, reconstituted in 0.2% formic acid/2% acetonitrile for the consequent analysis by LC-MS).

Notes:
7. After each centrifugation step make sure that all added solution has gone through the Cys-STrap tip.
8. The typical working ratio between the STrapping buffer in the Cys-STrap tip and the acidified sample is 6:1.

REFERENCES

1 Wisniewski, J. R., Zougman, A. & Mann, M. Combination of FASP and StageTip-based fractionation allows in-depth analysis of the hippocampal membrane proteome. *J Proteome Res* 8, 5674-5678, doi:10.1021/pr900748n (2009).
2 Rappsilber, J., Mann, M. & Ishihama, Y. Protocol for micro-purification, enrichment, pre-fractionation and storage of peptides for proteomics using StageTips. *Nature protocols* 2, 1896-1906, doi:10.1038/nprot.2007.261 (2007).

Targeted Peptide Enrichment with STrap

Figure 11:
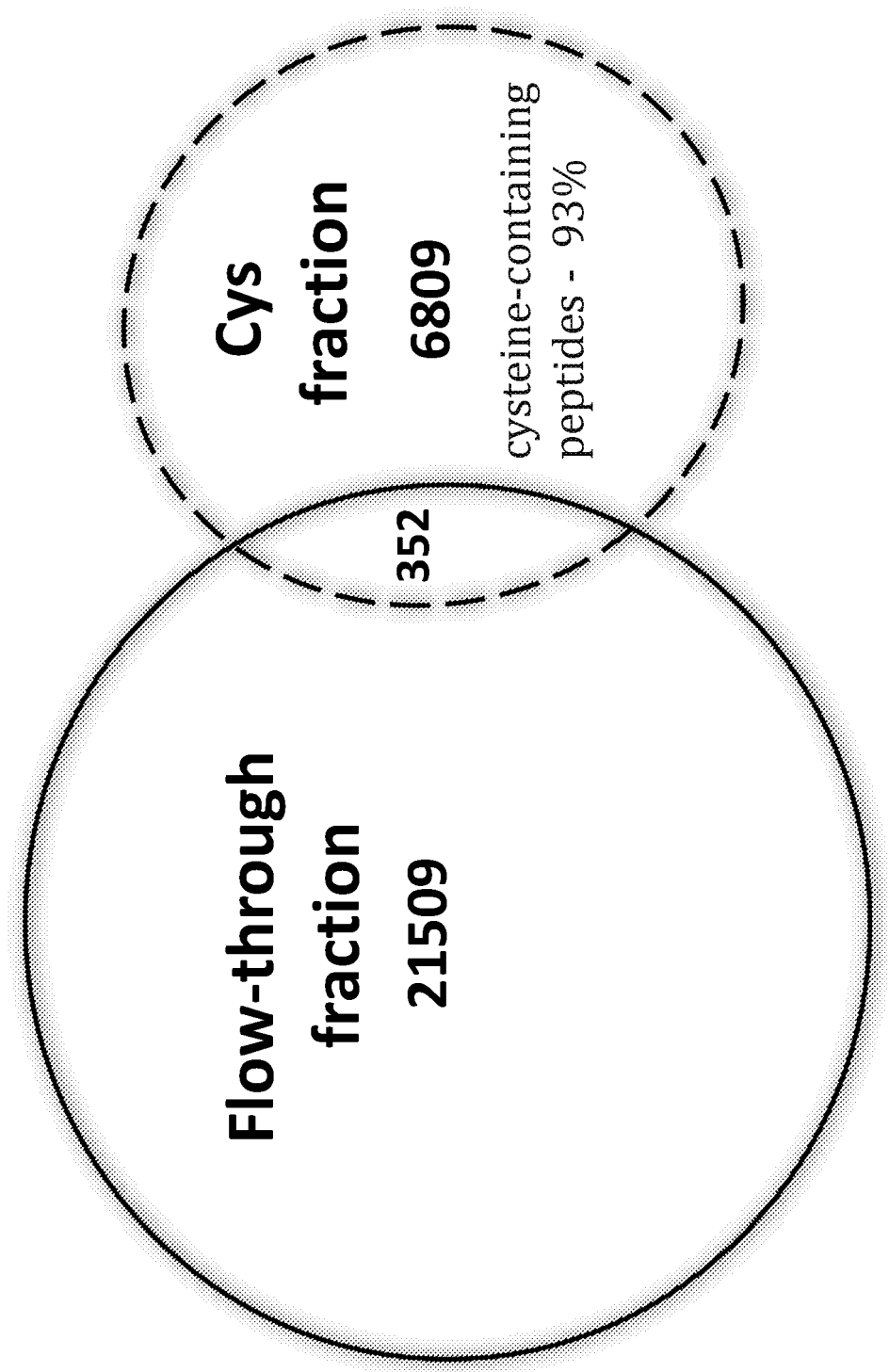
FIG. 11. Cys-STrap proteomics analysis of the MGH-U3 cell lysate. The Venn diagram shows the peptide numbers identified by mass spectrometry in each of the distinct digest fractions.

If the depth filter surface is silica-based, it is easily modifiable with functional groups based on the silane chemistry. Thus, during the digest, peptides possessing targeted features could be captured/enriched in the STrap unit. As an example, the quartz depth filter could be activated with the pyridyldithiol group (via consecutive reactions with (3-Aminopropyl)triethoxysilane and N-succinimidyl 3-(2-pyridyldithio)propionate) enabling the capture of the cysteine containing peptides. In this case, the modified STrap unit contains only the depth-filter part. The protein particulate is captured and digested in the depth filter. The cysteine-containing peptides are covalently attached to the quartz surface during the digest, the uncaptured peptides are eluted into the collecting tube for the downstream processing (e.g. further fractionation steps such as strong-anion exchange, reversed-phase clean up and downstream analysis), the STrap unit is washed rigorously and the cysteine-containing peptides are eluted using a reducing agent such as dithiothreitol, for example, alkylated and cleaned up for further analysis. An example of the output of the cysteine enrichment STrap (Cys-STrap) method applied to the bottom-up proteomics profiling of the MGH-U3 bladder cancer cell line according to the provided Cys-STrap protocol is presented in FIG. 11. We can observe the separation of the peptide products into two distinct populations—the flow-through (21509 peptides, 98% unique) and cysteine-enriched (6809 peptides, 95% unique, 93% cysteine-containing). The proposed concept is not limited to the cysteine peptide enrichment only and could be used with other molecular probes targeting either specific amino acids or amino acid modifications, e.g. the filter could be derivatized with (3-Glycidyloxypropyl)trimethoxysilane and then $NH_2$-modified aptamer ligands could be covalently attached to the silica surface (e.g. such as the aptamers against L-Arginine[1] to enrich for Arginine-containing peptides) or, by the same token, the filter could be functionalized with aminophenylboronic acid[2] to enrich for glycopeptides.

REFERENCES

1 Harada, K. & Frankel, A. D. Identification of two novel arginine binding DNAs. *The EMBO journal* 14, 5798-5811 (1995).
2 Weith, H. L., Wiebers, J. L. & Gilham, P. T. Synthesis of cellulose derivatives containing the dihydroxyboryl group and a study of their capacity to form specific complexes with sugars and nucleic acid components. *Biochemistry* 9, 4396-4401 (1970).

Serum Processing with STrap

Figure 12:
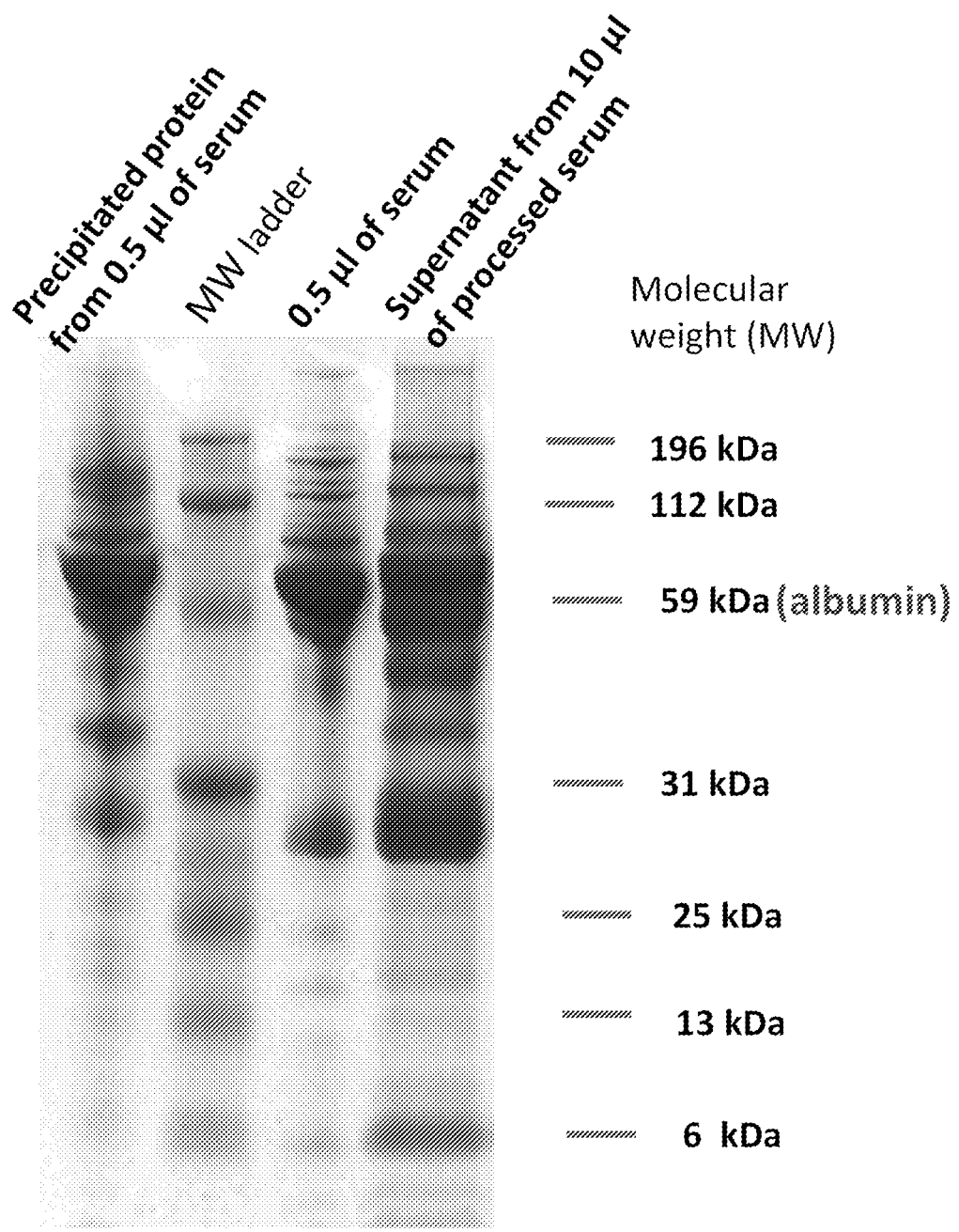
FIG. 12. Serum preparation for the downstream processing with the STrap methodology. We observe removal of the major portion of serum albumin in the precipitated fraction. The supernatant is taken for further processing with the Cys-STrap method.

The application is based on the observation that in ~2% reducing Sodium Dodecyl Sulfate (SDS) solution and upon acidification with phosphoric acid some abundant serum proteins, such as albumin, are precipitated out of the solution (FIG. 12), thus allowing direct proteomics analysis of the acidified SDS-solubilized serum samples based on the STrap principles (e.g. using the Cys-STrap method) without employing preliminary serum depletion procedures, which are typically performed in order to remove abundant serum proteins that severely interfere with identification of the low abundant proteins by mass spectrometry. Using the processing protocol outlined below in combination with the Cys-STrap method we have identified ~370 proteins in a normal human serum sample, which is an increase of ~2 times in protein identifications over a typical proteomics profiling of the undepleted serum.

Serum Processing with Modified STrap Protocol (Outline)
1. To 10 µl of serum add 10 µl of the reducing SDS solution (4.5 (w/v) sodium dodecyl sulfate, 50 mM Tris/HCl pH 7.5, 40 mM dithiothreitol)
2. Heat the sample for 7 min at 95° C. in the heating block
3. Remove the sample from the heating block and incubate for 20 min at room temperature (RT)
4. To the sample add 2.5 µl of 12.15% phosphoric acid
5. Centrifuge the sample at −12,000×g for 10 min
6. Carefully collect the supernatant for further processing with the Cys-STrap method Discussion of Depth Filters Relevant for the Present Invention Depth filters have a random network of pore channels that vary in size and geometry. They are manufactured from a variety of solid materials. Materials of construction include various forms of plastics, cellulose, and glass, either singly or in combination. The processes used to manufacture depth filters do not result in a regular arrangement of the solid matrix. Instead, there is a range of pore sizes within a given structure that includes pores significantly larger and significantly smaller than the pore rating.

The randomness of the structure does not allow the assignment of a definitive upper limit on the size of particles that may pass through the filter. A portion of the particles in the filtrate will exceed the pore rating. Depth filters also can entrap a large percentage of particles smaller than the pore rating. Because depth filters trap particles throughout the structure, they typically exhibit a high particle-handling capacity. This makes them particularly useful in applications where the solution being filtered has a high particle load. Depth filters are not considered sterilizing-grade.

FIG. 9 shows the results of comparison of various grades of flat filters, i.e. Grade 4 (20-25 µm), Grade 598 (8-10 µm) and Grade 3 (6 µm). Ten microgram of HeLa SDS lysate were acidified and precipitated in the neutral methanolic solution according to the STrap protocol and passed through the two layers of a filter paper stacked in a pipette tip. The trapped protein material was eluted with 2× sample loading buffer and visualized with the use of the Coomassie-stained polyacrylamide gel.

As can be seen, all three filters achieved some degree of retention, but the finer Grade 3 flat filter (6 µm cut-off) provided significantly improved performance and is able to retain about 50% of the loaded material. Thus the indication is that depth filters in the trapping range of from 10 µm down to 0.1 µm (or even smaller) are preferred, e.g. about 5 µm or finer, about 1 µm or finer, about 0.5 µm or finer being suitable.

Depth filters are typically used as pre-filters because they are an economical way to remove 98% of suspended solids and protect elements downstream from fouling or clogging. They owe their high capacity to the fact that contaminants are trapped and retained within the whole filter depth.

Conventional depth filters can be made out of the following materials:
Quartz
Glass Fibre
Polymers
Cellulose
Quartz Filter media made of pure micro-quartz fibres. Such media can be produced with or without glass fibres and binder. Media without glass fibres and binder are particularly appropriate for emission control at high temperatures of 900-950° C. and wherever absolute purity of the filter medium is required. Excellent filtration properties, minimal metal contents, outstanding weight and dimension stability. Examples in include MK360 (Munktell), a preferred filter material for the present invention.

Glass Fibre

As implied by the name, glass fibre depth filters are made from glass fibres. In sheet form the fibres are initially held together only as a consequence of mechanical interaction. To improve the handling characteristics, the filter is sometimes treated with a polymeric binder, such as polyvinyl alcohol, which serves to hold the matrix together. Glass fibre filters are also prone to fibre shedding. If required, a membrane filter can be placed downstream to retain any fibres. Examples include GF/D (Whatman), a filter material which is utilised in the above-mentioned examples.

Polymers

Polymeric depth filters are manufactured from plastic fibres of various lengths, morphologies, and diameters. To improve the strength of these filters and reduce the level of fibre shedding, the filter can be calendered, the process of running the material between cylindrical rollers to apply pressure and/or heat. Most polymeric depth filters are inherently hydrophobic. For low pressure aqueous filtration, the filter may require a surface treatment to render it wettable. Polymeric depth filters are normally very strong and easy to handle.

Cellulose

As implied by the name, cellulosic depth filters are made from cellulose fibres. The fibres can be derived from a relatively crude source, such as wood pulp, or a highly purified source, such as cotton. The filters are manufactured by techniques very similar to paper manufacture and are very economical. Although they are generally very easy to handle when dry, they are mechanically very weak when wet. Cellulosic filters are prone to fibre shedding during fabrication into a device and when used in filtration. If required, a membrane filter can be placed downstream to retain any fibres. Typically cellulose fibres are less preferred for the present invention, primarily due to the potential for contaminants and possible reaction with the proteins of the sample. However, certain highly purified forms may well be useful.

REFERENCES

1. Zhang, Y., Fonslow, B. R., Shan, B., Baek, M. C. & Yates, J. R., 3rd Protein Analysis by Shotgun/Bottom-up Proteomics. *Chem Rev* 113, 2343-2394 (2013).

2. Yu, Y. Q., Gilar, M., Lee, P. J., Bouvier, E. S. & Gebler, J. C. Enzyme-friendly, mass spectrometry-compatible surfactant for in-solution enzymatic digestion of proteins. *Anal Chem* 75, 6023-6028 (2003).

3. Kadiyala, C. S., Tomechko, S. E. & Miyagi, M. Perfluorooctanoic acid for shotgun proteomics. *PLoS One* 5, e15332 (2010).

4. Summers, D. F., Maizel, J. V., Jr. & Darnell, J. E., Jr. Evidence for virus-specific noncapsid proteins in poliovirus-infected HeLa cells. *Proc Natl Acad Sci USA* 54, 505-513 (1965).

5. Laemmli, U. K. Cleavage of structural proteins during the assembly of the head of bacteriophage T4. *Nature* 227, 680-685 (1970).

6. Shevchenko, A., Wilm, M., Vorm, O. & Mann, M. Mass spectrometric sequencing of proteins silver-stained polyacrylamide gels. *Anal Chem* 68, 850-858 (1996).

7. Wisniewski, J. R., Zougman, A., Nagaraj, N. & Mann, M. Universal sample preparation method for proteome analysis. *Nat Methods* 6, 359-362 (2009).

8. Havlis, J., Thomas, H., Sebela, M. & Shevchenko, A. Fast-response proteomics by accelerated in-gel digestion of proteins. *Anal Chem* 75, 1300-1306 (2003).

9. Zhou, H., Ning, Z., Wang, F., Seebun, D. & Figeys, D. Proteomic reactors and their applications in biology. *Febs J* 278, 3796-3806 (2011).

10. Gilar, M., Olivova, P., Daly, A. E. & Gebler, J. C. Two-dimensional separation of peptides using RP-RP-HPLC system with different pH in first and second separation dimensions. *J Sep Sci* 28, 1694-1703 (2005).

11. Nagaraj, N. et al. Deep proteome and transcriptome mapping of a human cancer cell line. *Mol Syst Biol* 7, 548 (2011).

12. Wisniewski, J. R. & Mann, M. Spin filter-based sample preparation for shotgun proteomics Reply. *Nat Methods* 6, 785-786 (2009).

13. Loyer, P. et al. Characterization of cyclin L1 and L2 interactions with CDK11 and splicing factors: influence of cyclin L isoforms on splice site selection. *J Biol Chem* 283, 7721-7732 (2008).

14. Bordier, C. Phase separation of integral membrane proteins in Triton X-114 solution. *J Biol Chem* 256, 1604-1607 (1981).

15. Wisniewski, J. R., Dus, K. & Mann, M. Proteomic workflow for analysis of archival formalin-fixed and paraffin-embedded clinical samples to a depth of 10 000 proteins. *Proteomics Clin Appl* 7, 225-233 (2013).

16. Di Palma, S., Mohammed, S. & Heck, A. J. ZIC-cHILIC as a fractionation method for sensitive and powerful shotgun proteomics. *Nat Protoc* 7, 2041-2055 (2012).

17. Cox, J. & Mann, M. MaxQuant enables high peptide identification rates, individualized p.p.b.-range mass accuracies and proteome-wide protein quantification. *Nat Biotechnol* 26, 1367-1372 (2008).

18. Cox, J. et al. Andromeda: a peptide search engine integrated into the MaxQuant environment. *J Proteome Res* 10, 1794-1805 (2011).

The invention claimed is:

1. A method of preparing a sample comprising one or more proteins of interest, the method comprising the ordered steps of:

providing a sample comprising a population of proteins of interest solubilized with sodium dodecyl sulfate (SDS) in a medium, wherein the proteins are not solubilized with urea;

shearing DNA in the sample, if the sample comprises cells;

reducing disulfides and alkylating cysteines in the sample;

exposing said sample to a precipitant, wherein said precipitant solubilizes the SDS, causes precipitation of said proteins as a suspension of particles of protein, does not render the precipitated proteins insensitive to protease digestion, and wherein the precipitant comprises phosphoric acid;

adding an aqueous methanolic solution to the sample containing the precipitated proteins;

during or after the precipitation step, bringing said sample into contact with a matrix that is a depth filter having a network of pore channels adapted to capture said precipitated protein particles throughout the depth filter, thereby preventing excessive aggregation of precipitated protein particles, and further wherein said matrix does not bind the solubilized SDS;

washing the matrix containing the captured precipitated protein particles with an aqueous methanolic solution to remove the SDS; and digesting the captured precipitated protein particles in situ using a protease.

* * * * *